US011878008B2

(12) United States Patent
Choi et al.

(10) Patent No.: US 11,878,008 B2
(45) Date of Patent: Jan. 23, 2024

(54) COMPOSITION FOR PREVENTING OR TREATING ATOPIC DERMATITIS

(71) Applicant: AMOREPACIFIC CORPORATION, Seoul (KR)

(72) Inventors: Gyeyoung Choi, Yongin-si (KR); Hyunjin Nam, Yongin-si (KR); Miyoung Park, Yongin-si (KR); Kyoungmi Jung, Yongin-si (KR); Jihae Lee, Yongin-si (KR); Chang Soon Choi, Yongin-si (KR); Youngho Park, Yongin-si (KR); Jong Hwa Roh, Yongin-si (KR); Eunsil Park, Yongin-si (KR); Jaehong Park, Yongin-si (KR); Kwanghyun Shin, Yongin-si (KR); Byoung Young Woo, Yongin-si (KR); Kiwha Lee, Yongin-si (KR); Wonkyung Cho, Yongin-si (KR); Joonho Choi, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 528 days.

(21) Appl. No.: 16/805,381

(22) Filed: Feb. 28, 2020

(65) Prior Publication Data

US 2020/0197379 A1 Jun. 25, 2020

Related U.S. Application Data

(63) Continuation-in-part of application No. PCT/KR2018/004328, filed on Apr. 13, 2018.

(30) Foreign Application Priority Data

Aug. 31, 2017 (KR) .................. 10-2017-0110669
Apr. 12, 2018 (KR) .................. 10-2018-0042816

(51) Int. Cl.
*A61P 17/04* (2006.01)
*A61K 31/44* (2006.01)
*A61K 9/00* (2006.01)

(52) U.S. Cl.
CPC ............ *A61K 31/44* (2013.01); *A61K 9/0014* (2013.01); *A61P 17/04* (2018.01)

(58) Field of Classification Search
CPC ..................................................... A61P 17/04
See application file for complete search history.

(56) References Cited

U.S. PATENT DOCUMENTS

2008/0312234 A1 12/2008 Kim et al.
2020/0197379 A1 6/2020 Choi et al.

FOREIGN PATENT DOCUMENTS

| KR | 101410318 B1 | 6/2014 |
| WO | 2007047575 A2 | 4/2007 |
| WO | 2008013414 A1 | 1/2008 |

OTHER PUBLICATIONS

Lee, Y.W., et al. "Efficacy and safety of PAC-14028 cream—a novel, topical, nonsteroidal, selective TRPV1 antagonist in patients with mild-to-moderate atopic dermatitis: a phase IIb randomized trial." British Journal of Dermatology. (2019), vol. 180, pp. 1030-1038. (Year: 2019).*
"Healing Foot Pain with Chinese Medicine." (Dec. 23, 2019). Emily Grace Acupuncture. Accessed Apr. 9, 2022. Available from: < Acupuncture for Plantar Fasciitis—Emily Grace Acupuncture > /. (Year: 2019).*
Yun, Jun-Won, et al. "TRPV1 antagonist can suppress the atopic dermatitis-like symptoms by accelerating skin barrier recovery." Journal of Dermatological Science (2011), vol. 62, pp. 8-15. (Year: 2011).*
Kyung-Min, et al. "Development of PAC-14028, a Novel Transient Receptor Potential Vanilloid Type 1 (TRPV1) Channel Antagonist as a New Drug for Refractory Skin Diseases." Arch Pharm Res. (2012), vol. 35, No. 3, pp. 393-396. (Year: 2012).*
Leshem, Y.A., et al. "What the Eczema Area and Severity Index score tells US about the severity of atopic dermatitis: an interpretability study." British Journal of Dermatology. (2015), vol. 172, pp. 1353-1357. (Year: 2015).*
"Visual Analogue Scale—Pruritus Resources." (Nov. 23, 2011), Accessed Nov. 1, 2022. Available from: < http://www.pruritussymposium.de/visualanaloguescale.html > . (Year: 2011).*
Wohlrab, Johannes. "Topical preparations and their use in dermatology." J. German Society of Dermatology. (2016), pp. 1061-1070. (Year: 2016).*
Eure, Marian Anne. "Routes of Medication Administration." (Apr. 18, 2016). Accessed Apr. 9, 2022. Available from: < How to Take Your Meds: Medication Administration Routes (verywellhealth.com) > . (Year: 2016).*
"Drug absorption through the skin: a mixed blessing." Archives of Disease in Childhood. (1987), vol. 62, pp. 220-221. (Year: 1987).*
Jia, Wei, et al. "Cataplasma of traditional Chinese medicine." Zhongguo Zhong Yao Za Zhi. Jan. 2003, 28(1): 7-11. (Year: 2003).*
Garg, Tarun, et al. "Comprehensive review on additives of topical dosage forms for drug delivery." Drug Delivery. (2015), vol. 22, Issue 8, pp. 969-987. (Year: 2015).*
International Search Report and Written Opinion for International application No. PCT/KR2018/004328, dated Jul. 24, 2018, 8 pages, ISA/KR.
Jin et al., Animal models of atopic dermatitis, Journal of Investigative Dermatology, 2009, pp. 31-40, vol. 129.
Ewald et al. Major differences between human atopic dermatitis and murine models, as determined by using global transcriptomic profiling, J Allergy Clin Immunol. 2017, pp. 562-571, vol. 139 No. 2.

(Continued)

*Primary Examiner* — John S Kenyon
(74) *Attorney, Agent, or Firm* — Lucas & Mercanti, LLP

(57) ABSTRACT

Disclosed is a method for preventing or treating atopic dermatitis using TRPV1 receptor antagonist. More specifically, it may be possible to prevent and/or treat the atopic dermatitis without any side effects such as an increase in body temperature, epidermal atrophy, and the like by percutaneously administrating a composition for external use on the skin containing the TRPV1 receptor antagonist.

16 Claims, 13 Drawing Sheets

(56) References Cited

OTHER PUBLICATIONS

Tanaka et al., Recent findings in mouse models for human atopic dermatitis, Japanese Association for Laboratory Animal Science, 2012, pp. 77-84, vol. 61, JP.
Leshem et al., What the EASI score tells us about the severity of atopic dermatitis—an interpretability study, British Journal of Dermatology, 2015, pp. 1353-1357, vol. 172, UK.
Alawi et al., The sympathetic nervous system is controlled by transient receptor potential vanilloid 1 in the regulation of body temperature. The FASEB Journal, 2015, pp. 4285-4298, vol. 29, US.
Ayoub et al., Answering the burning question of how transient receptor potential vanilloid-1 channel antagonists cause unwanted hyperthermia, Pharmacological Reviews, 2009, pp. 225-227, vol. 61 No. 3, US.
Pasparakis et al., Mechanisms regulating skin immunity and inflammation. Nature Reviews, May 2014, pp. 289-301, vol. 14.
Hay et al., Clinical development success rates for investigational drugs, Nature Biotechnology, Jan. 2014, pp. 40-51, vol. 32.
Waring et al., An analysis of the attrition of drug candidates from four major pharmaceutical companies, Nature Reviews Drug Discovery, Jun. 2015, pp. 1-12, vol. 14.
Pang, D. J. et al., Understanding the complexity of gammadelta Tcell subsets in mouse and human, Immunology, 2012, pp. 283-290, vol. 136.
Zollner et al., Acute and chronic models of allergic contact dermatitis: advantages and limitations. Ernst Schering Res Found Workshop, 2005, pp. 255-275.
Tarayre et al. Comparative actions of immunosuppressants, glucocorticoids and non-steroidal anti-inflammatory drugs on various models of delayed hypersensitivity and on a non-immune inflammation in mice, Arzneimittel-forschung, 1990.
Queille-Roussel, C. et al., SDZ ASM 981 is the first non-steroid that suppresses established nickel contact dermatitis elicited by allergen challenge, Contact Dermatitis, 2000, pp. 349-350, vol. 42.
Byung Eui Kim et al., TNF-alpha downregulates filaggrin and loricrin through c-Jun N-terminal kinase: role for TNF-alpha antagonists to improve skin barrier, Journal of Investigative Dermatology, 2011, pp. 1272-1279, vol. 131.
Perera, G. K. et al., Psoriasis. The Annual Review of Pathology: Mechanisms of Disease, 2012, pp. 385-422, vol. 7.
Wagner, E. F. et al., Psoriasis: what we have learned from mouse models, Nature Reviews Rheumatology, 2010, 6, pp. 704-714, vol. 6.
Yang-Hui Park et al., Oral and topical pharmacokinetic studies of a novel TRPV1 antagonist, PAC-14028 in rats and minipigs using liquid chromatography/tandem mass spectrometric method, Journal of Pharmaceutical and Biomedical Analysis, 2012, pp. 8-14, vol. 61.
Kyung-Min Lim et al., Development of PAC-14028, a Novel Transient Receptor Potential Vanilloid Type 1 (TRPV1) Channel Antagonist as a New Drug for Refractory Skin Diseases, Archives of Pharmacal Research, 2012, pp. 393-396, vol. 35 No. 3.
Jun-Won Yun et al., TRPV1 antagonist can suppress the atopic dermatitis-like symptoms by accelerating skin barrier recovery, Journal of Dermatological Science, 2011, pp. 8-15, vol. 62.
Jun-Won Yun et al., Antipruritic Effects of TRPV1 Antagonist in Murine Atopic Dermatitis and Itching Models, The Journal of Investigative Dermatology, 2011, pp. 1576-1579, vol. 131.
Chang et al., "Mechanism of sleep disturbance in children with atopic dermatitis and the role of the circadian rhythm and melatonin", Int'l Journal of Molecular Sciences, 2016, vol. 17(4):462.
Ozawa et al., "Neuroselective transcutaneous electrical stimulation reveals neuronal sensitization in atopic dermatitis", The American Academy of Dermatology, 2009, pp. 609-614, vol. 60.
Yung-Sen Chang et al., "Atopic Dermatitis, Melatonin, and Sleep Disturbance", Pediatrics, 2014, pp. e397-e405, vol. 134.
Wilkowska et al., "Evaluation of safety and efficacy of Dermaveel in treatment of atopic dermatitis", Alergologia Polska—Polish Journal of Allergology, 2015, vol. 2, pp. 128-133.
"Sleep Disorders", Medline Plus, https://medlineplus.gov/sleepdisorders.html, 2021, pp. 1-8.
D.M. Paton, "Crisaborole: Phosphodiesterase inhibitor for treatment of atopic dermatitis," Drugs of Today, 2017, 53(4): 239-245.
Anonymous: "A Study to Evaluate the Safety and Efficacy of PAC-14028 Cream in Atopic Dermatitis," Internet, Oct. 21, 2015, Retrieved from the Internet: URL:https://beta.clinicaltrials.gov/study/NCT02583022.
European Patent Office, Office Action issued for the related European patent application No. 18851058.0, dated Feb. 22, 2023, 6 pages.

* cited by examiner

[FIG. 1A]
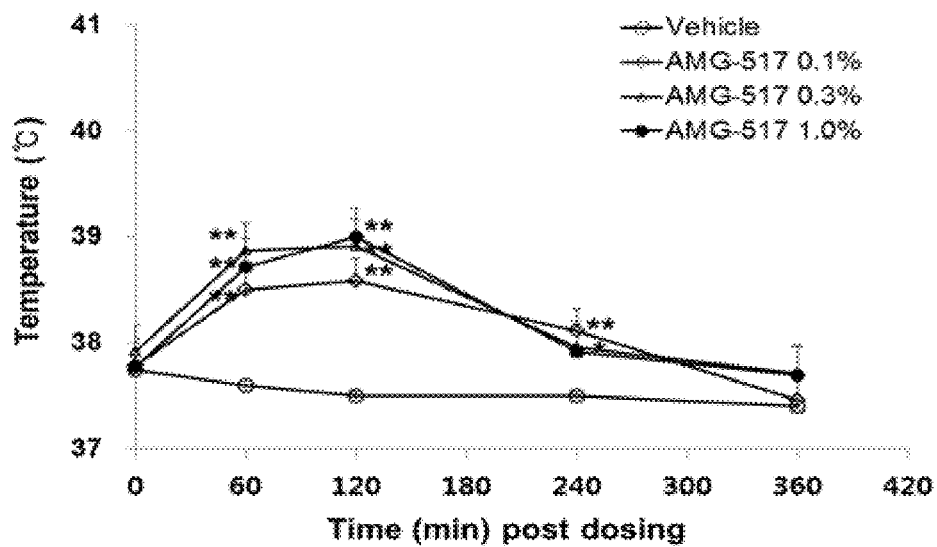
[FIG. 1B]
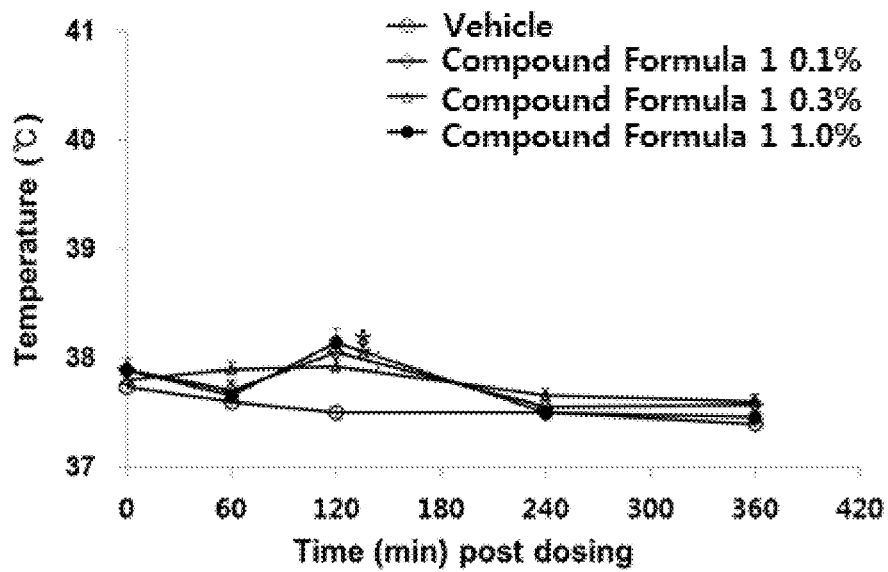

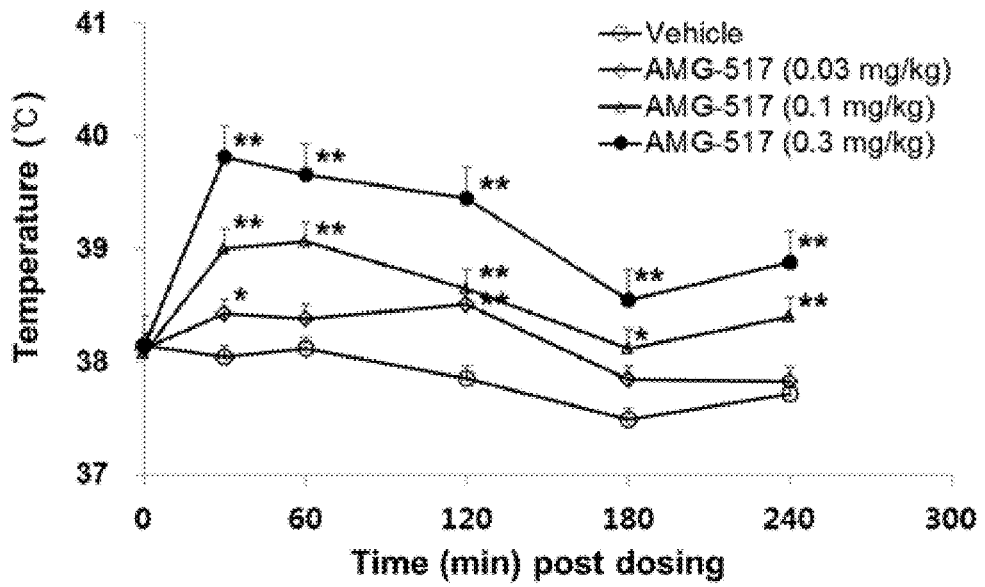
[FIG. 2A]
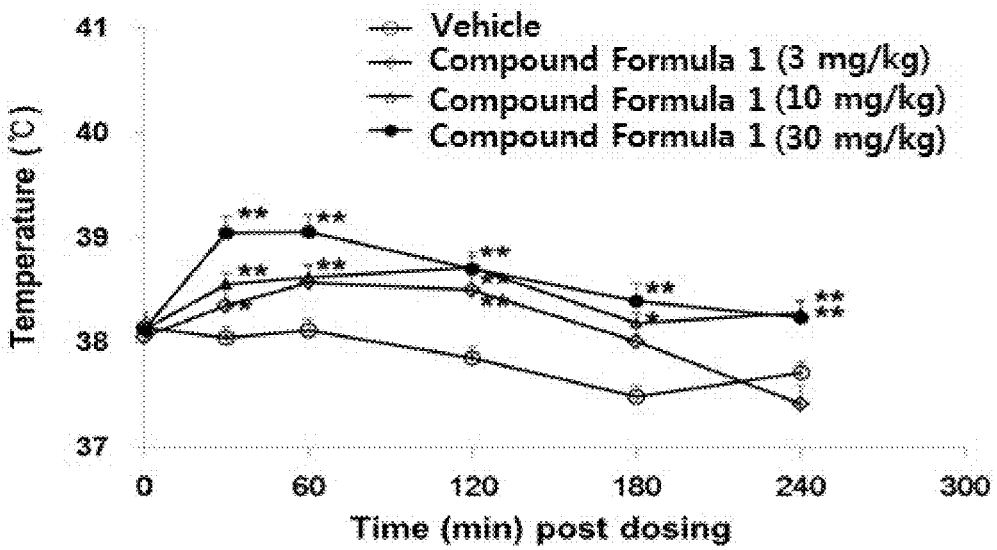
[FIG. 2B]

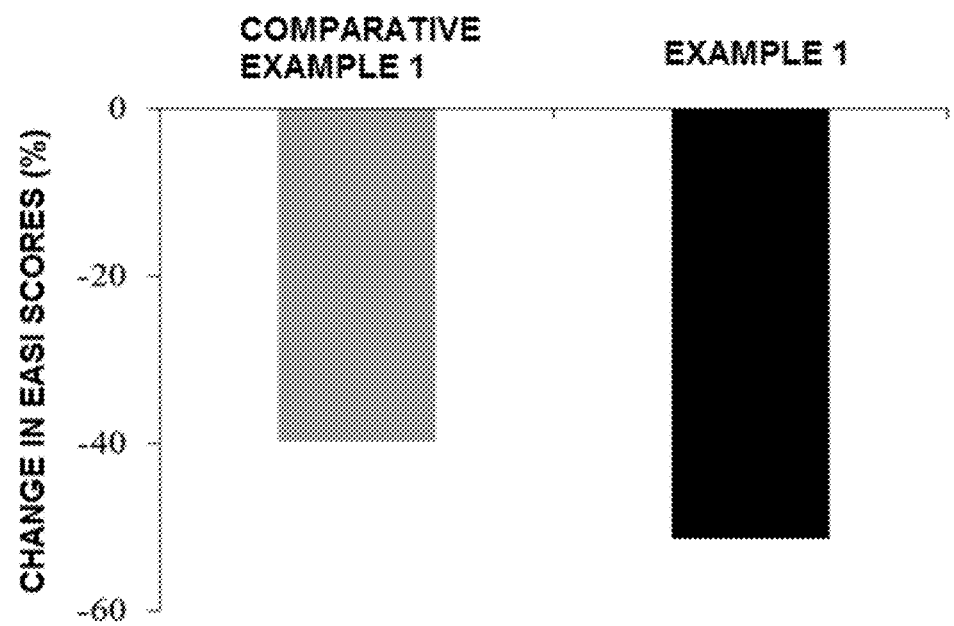
[FIG. 3A]
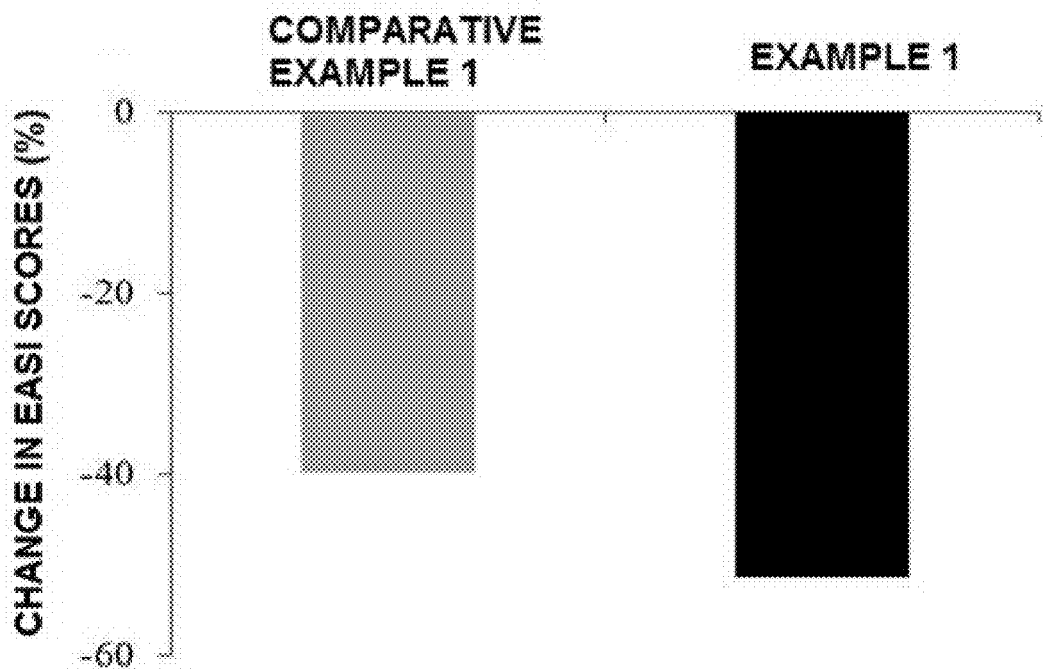
[FIG. 3B]

[FIG. 3C]
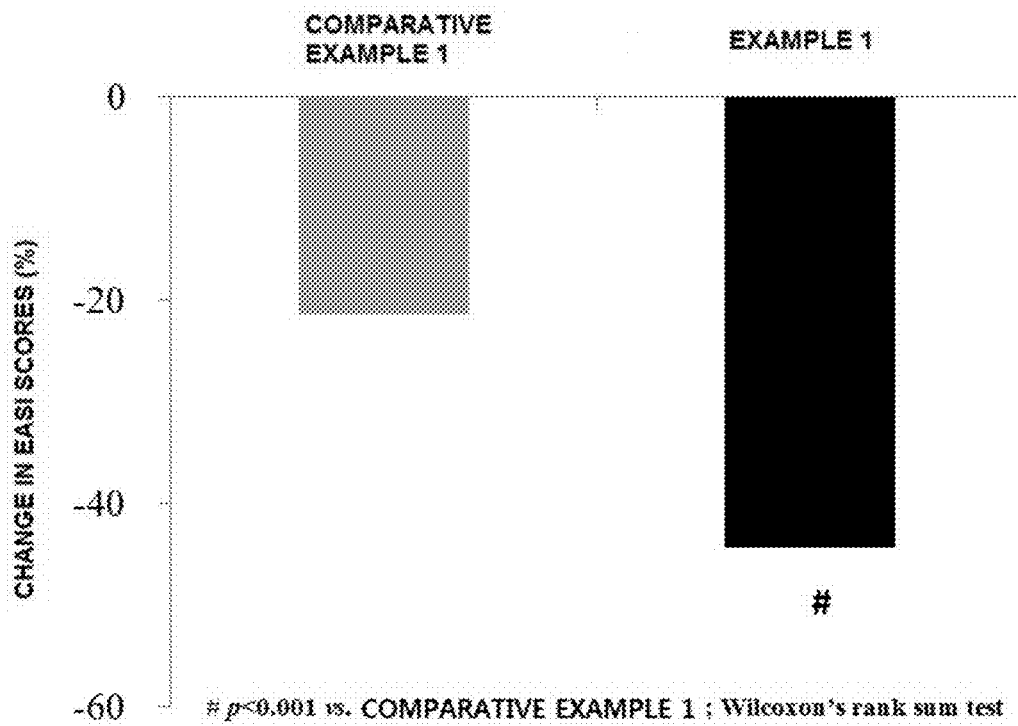
[FIG. 3D]
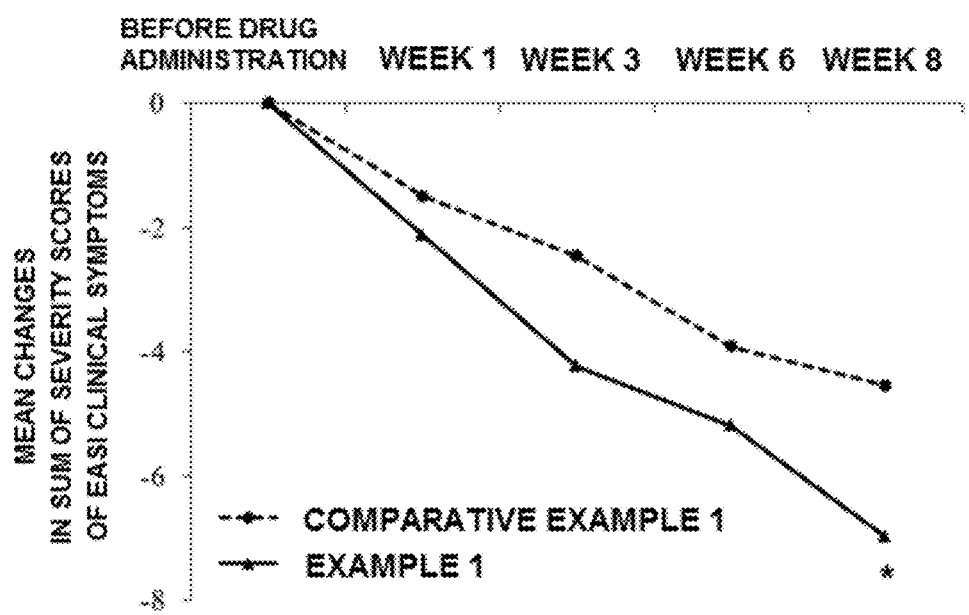

[FIG. 4A]
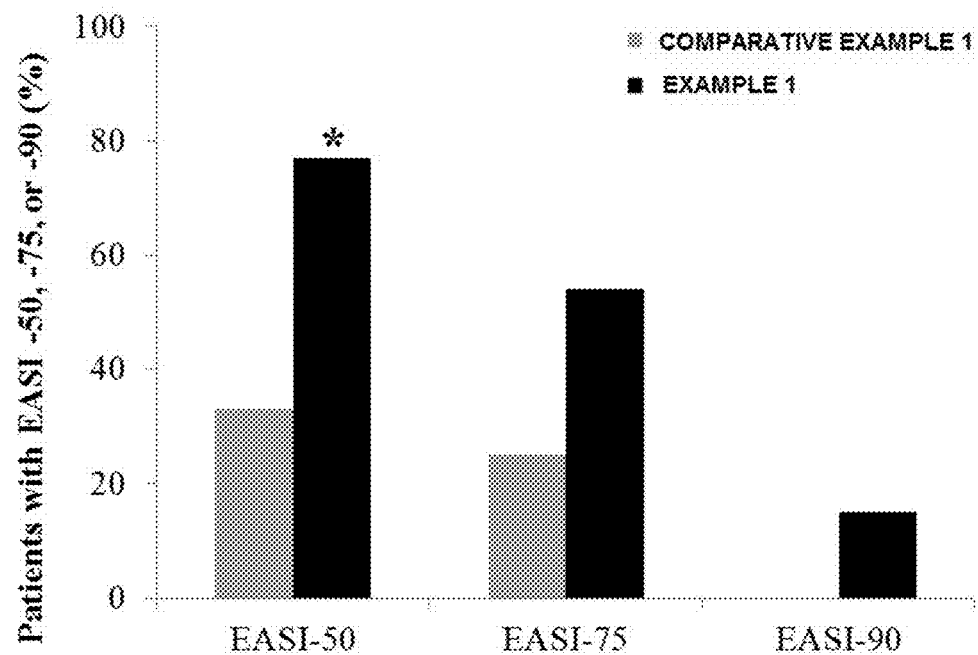
[FIG. 4B]
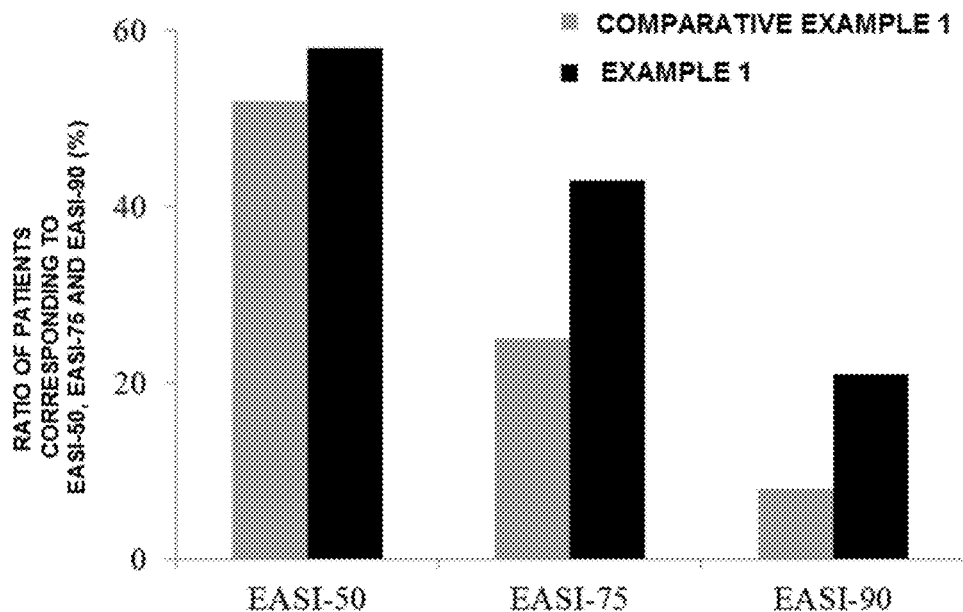

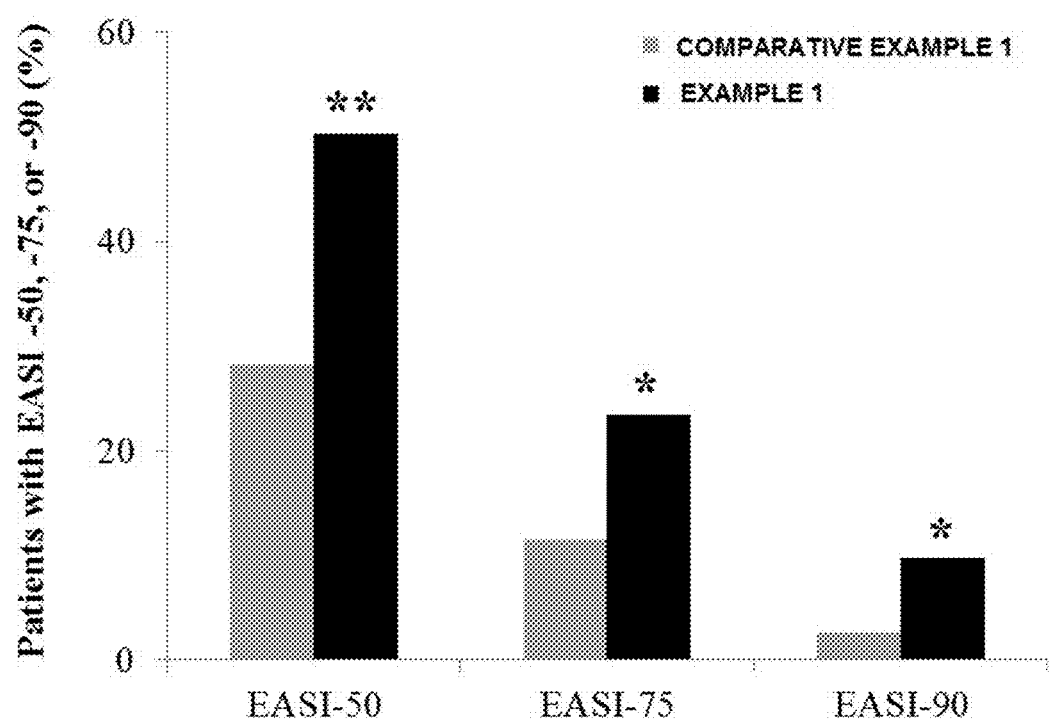

[FIG. 5A]
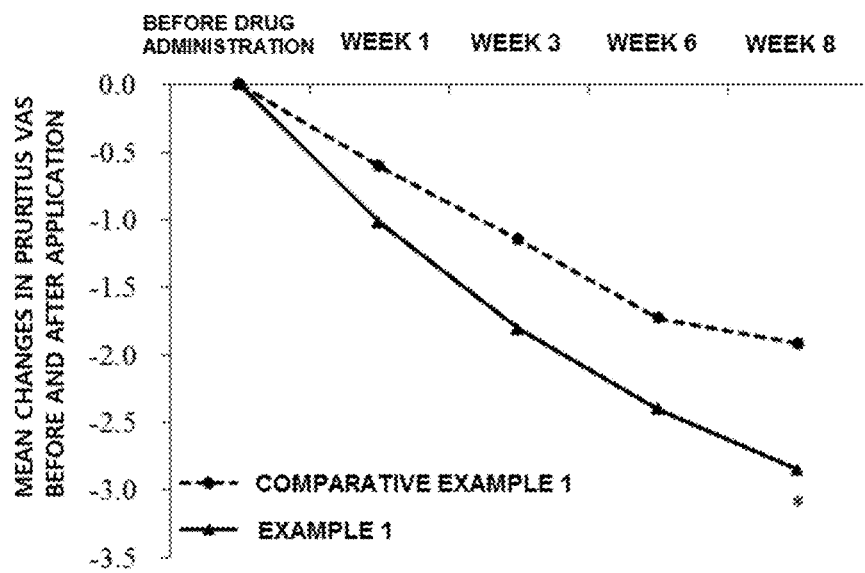
[FIG. 5B]
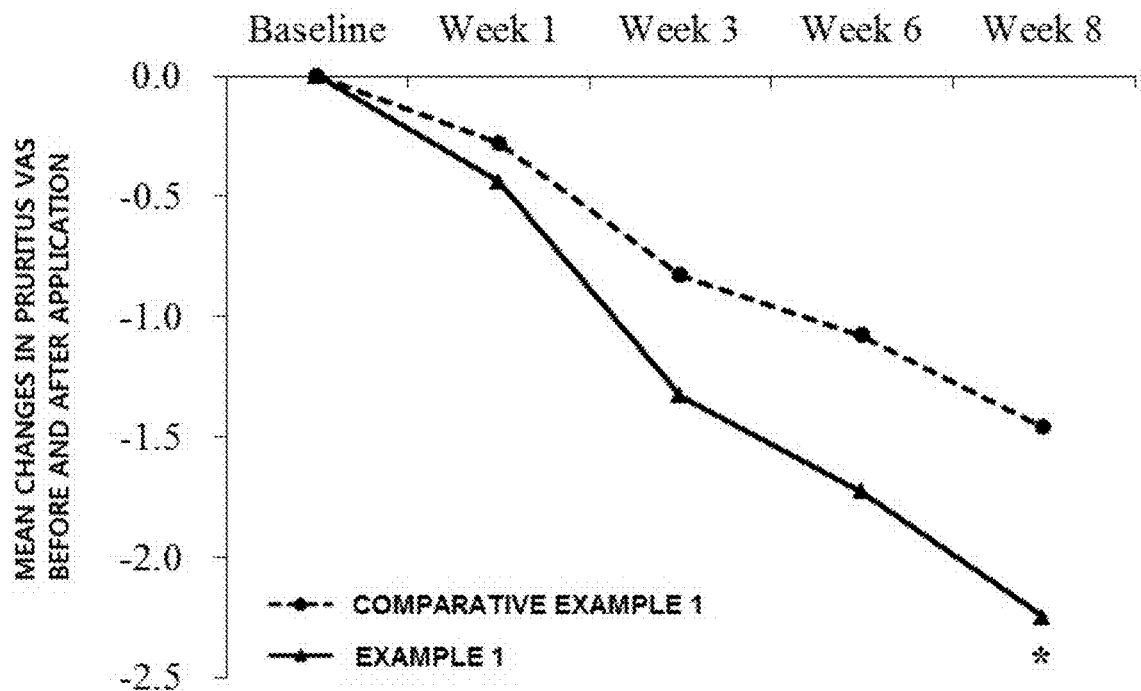

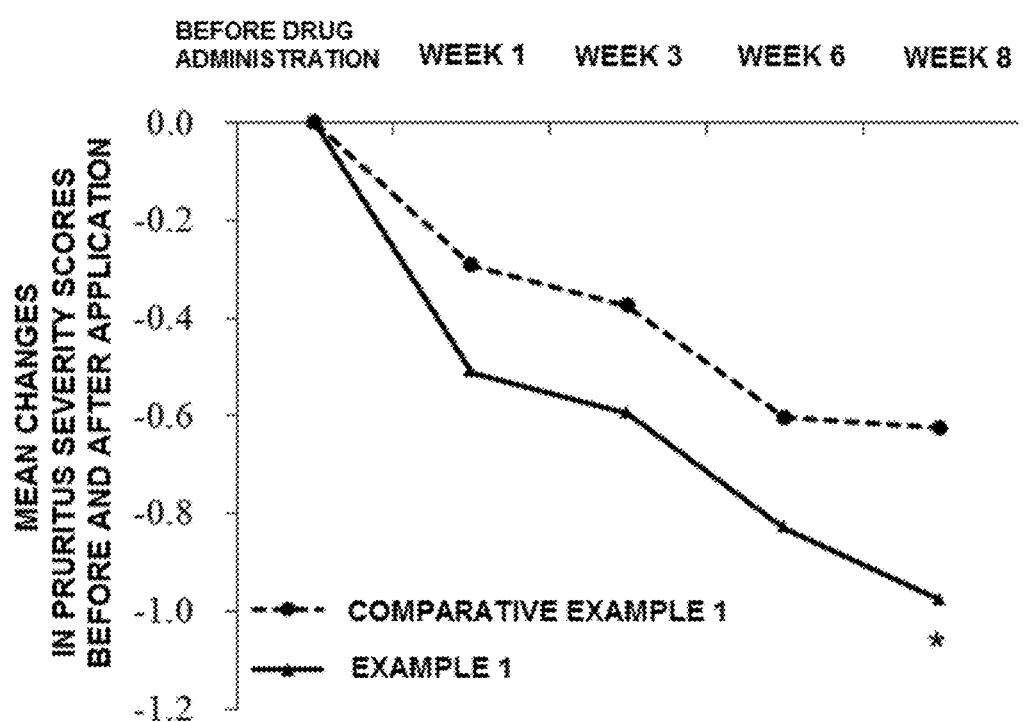
[FIG. 5C]

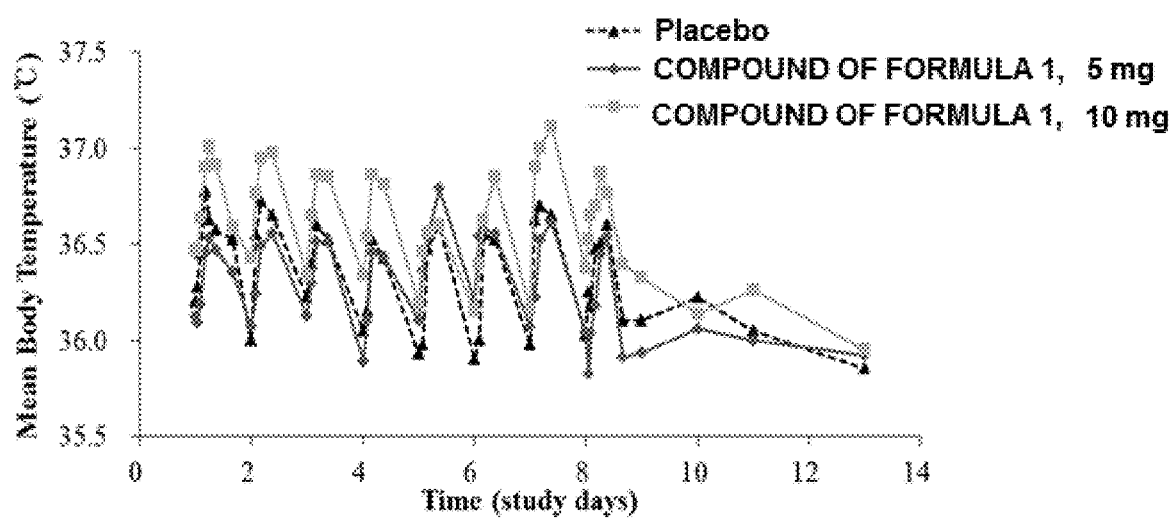
[FIG. 6A]
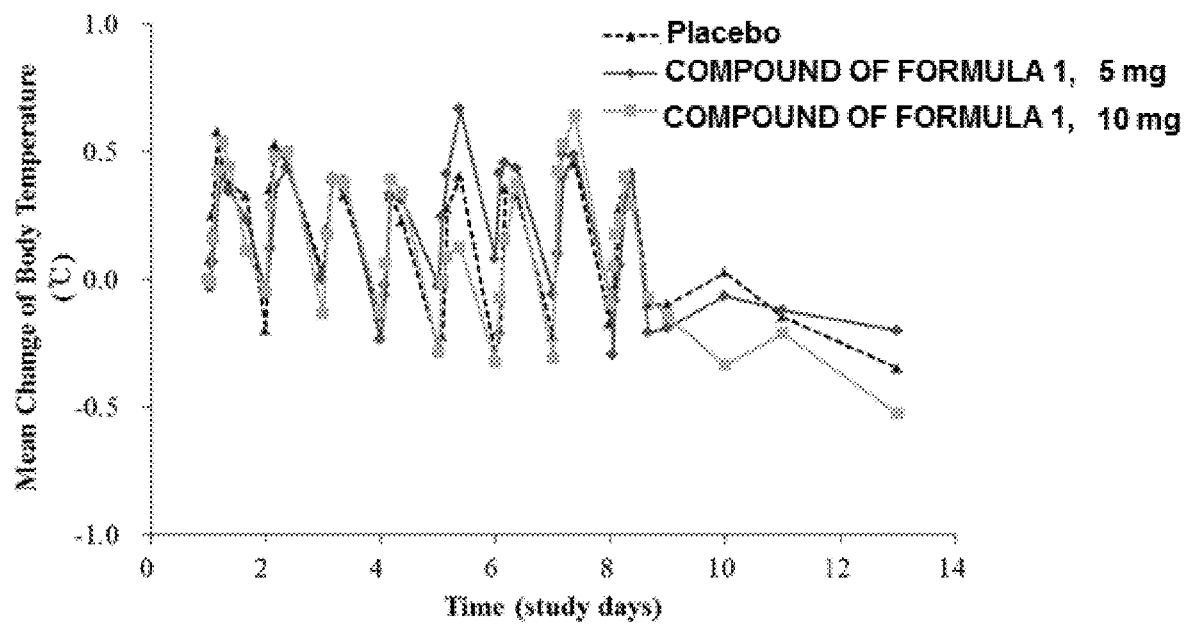
[FIG. 6B]

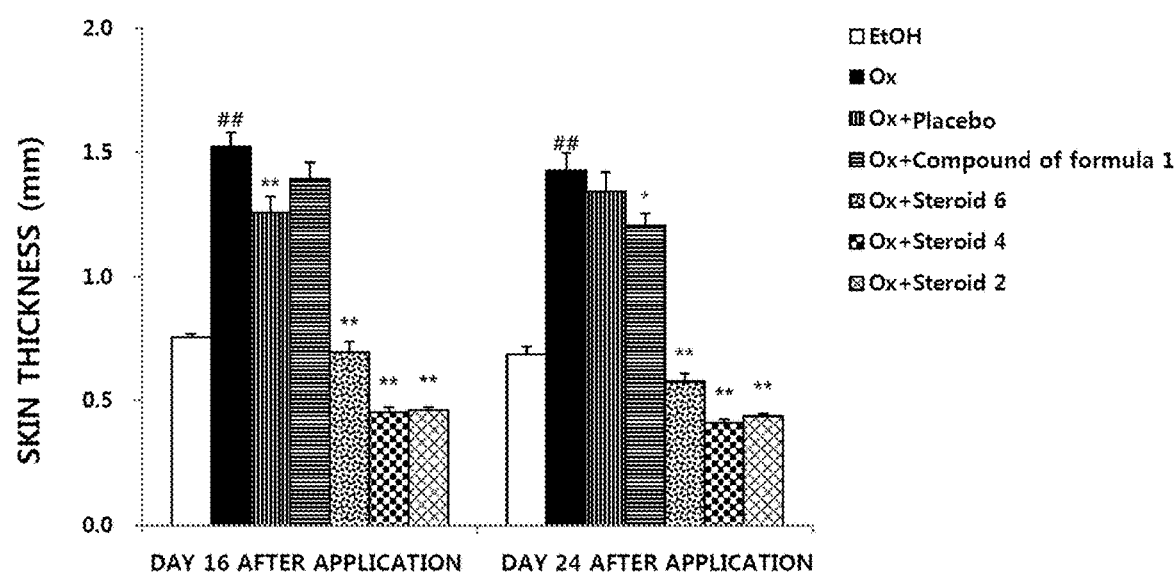

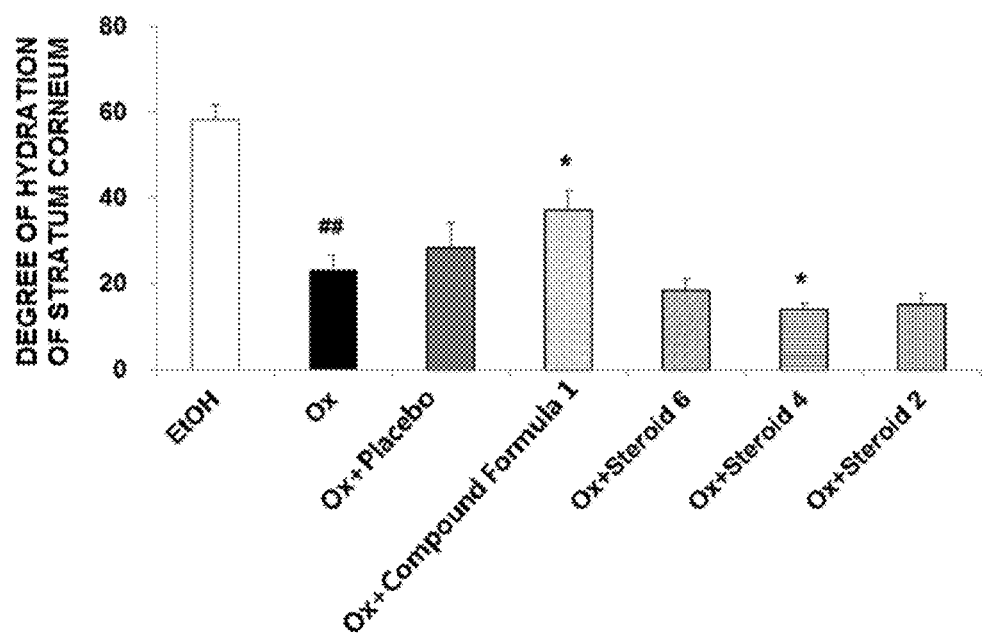
[FIG. 8]

[FIG. 9A]
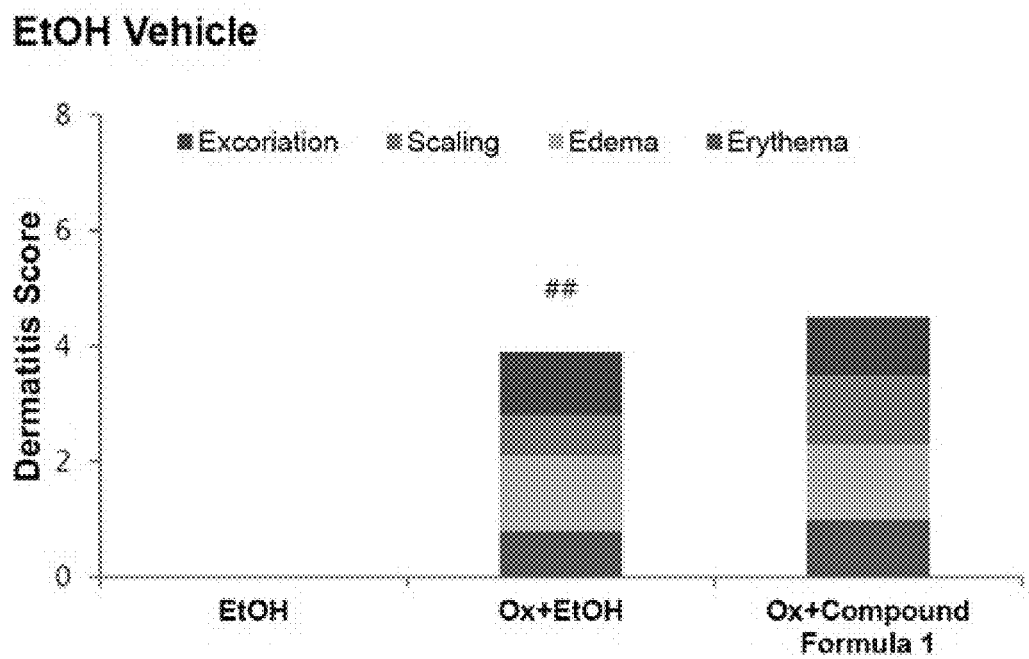
[FIG. 9B]
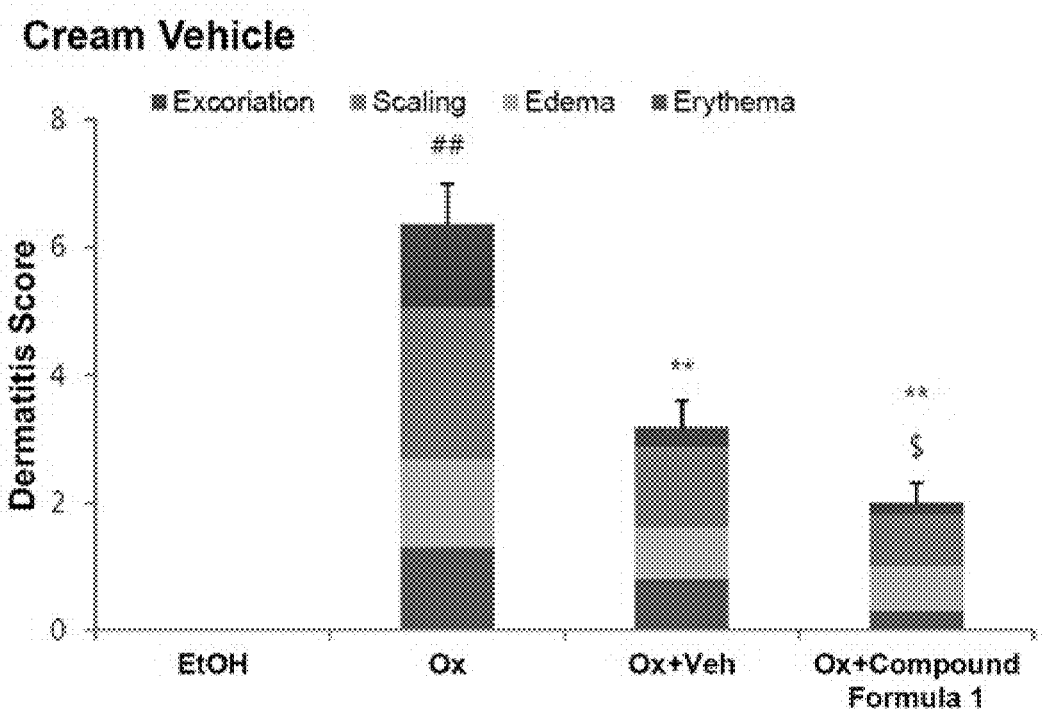

[FIG. 10A]
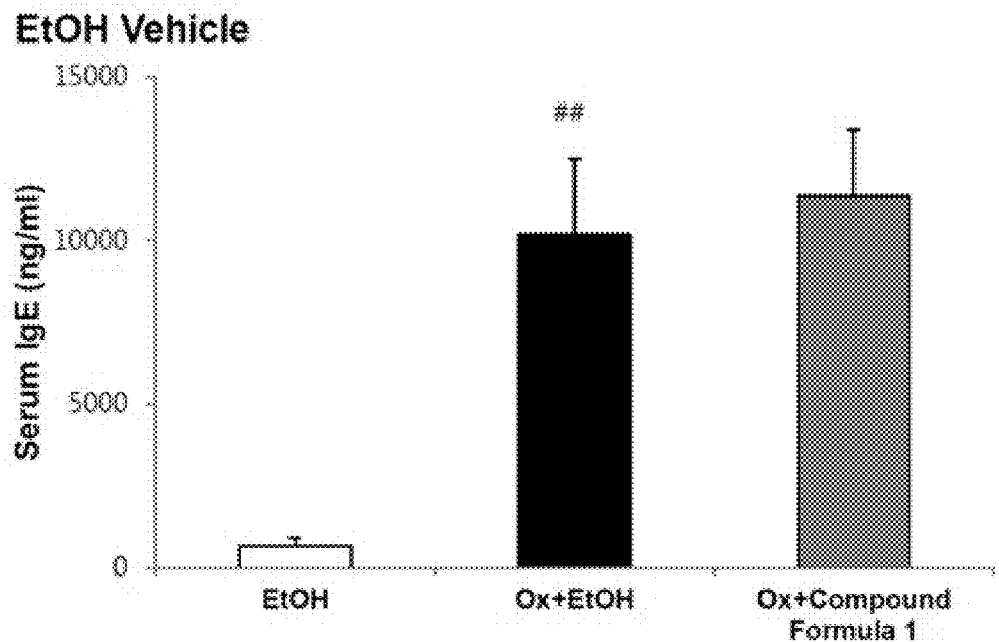
[FIG. 10B]
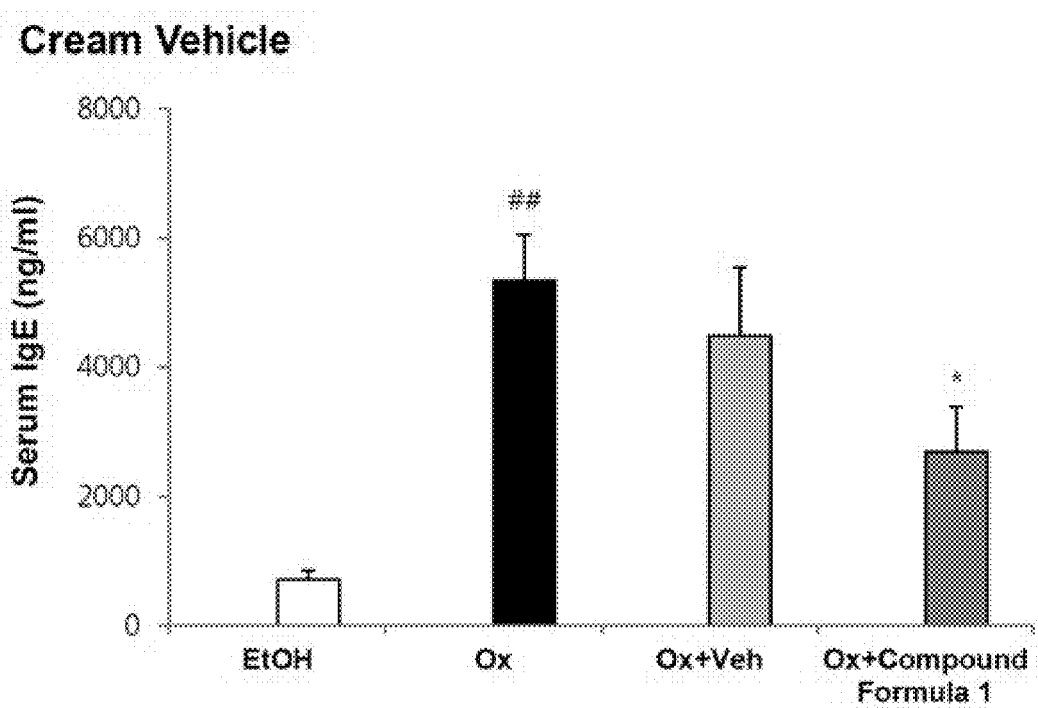

COMPOSITION FOR PREVENTING OR TREATING ATOPIC DERMATITIS

CROSS-REFERENCE TO RELATED APPLICATION

This application is continuation-in-part of PCT/KR2018/004328, filed Apr. 13, 2018 which claims the priority from Korean Patent Application No. 10-2017-0110669, filed Aug. 31, 2017, and Korean Patent Application No. 10-2018-0042816 filed Apr. 12, 2018, the contents of each of which are incorporated herein by reference.

BACKGROUND

Technical Field

The present invention relates to a method for preventing and/or treating atopic dermatitis using TRPV1(Transient receptor potential vanilloid subfamily, member 1) antagonist compound.

Background Art

Atopic dermatitis (AD) is a chronic and recurrent eczematous disease whose cause is not yet known, and is estimated to occur as a result of complex interaction between various factors such as genetic predispositions, impaired immune systems, skin barrier functions, environmental factors, and the like.

The representative clinical characteristics of AD include severe pruritus, dry and dead skin and eczema eruption. Particularly, severe cases of the disease may cause serious psychological problems and degradation in quality of life, which may lead to high social and economic losses. Corticosteroid drugs, antihistaminic drugs, immunosuppressants, and the like have been used to treat atopic dermatitis. However, such therapeutic agents have side effects or provide a temporary and incomplete relief of symptoms. Particularly, patients with moderate atopic dermatitis can become resistant to topical corticosteroid therapies. Therefore, an effective therapy for treating and/or preventing atopic dermatitis is needed.

To evaluate an effect of drugs for disease research or development of drugs to treat diseases, or to expect an effect of the drugs when clinically administered, a nonclinical trial using an animal model is generally performed prior to clinical trials. However, since the cause of atopic dermatitis is not yet known and is estimated to occur as a result of complex interaction between the various factors as described above, there is a limit in establishing an animal model for atopic dermatitis. Therefore, in the case of atopic dermatitis, there is no alternative but to typically use animal models such as a sensitization model in which AD is induced by applying sensitizing substances (i.e., haptens) or house dust mites on the skin, a genetic modification model in which a certain gene is artificially overexpressed or removed, or a spontaneous model in which AD is induced when certain laboratory animal species (i.e., NC/Nga, NOA mice) are naturally exposed to sensitizing substances or microbes in the air (Jin et al., Animal models of atopic dermatitis. J Invest Dermatol, 2009 (18), 129, 31-40). The limitations of such nonclinical trials(in vivo) were verified from the results of joint research of Rockefeller University, Kyoto University and LEO Pharma. This research demonstrates that the transcriptomes of IL-23-injected, NC/Nga, and oxazolone-challenged models, among various atopic dermatitis-like animal models, have the largest homology when compared with human meta-analysis-derived AD transcriptome, but have low homology values of 37%, 18%, and 17%, respectively. Further, it is demonstrated that the IL-23-injected and NC/Nga models induce an immune response through the TH1, TH2 and TH17 activities, and the oxazolone-challenged model induces an immune response through the TH1 activities. This indicates that the same drugs have different effects depending on the animal experiment models (Ewald et al., Major differences between human atopic dermatitis and murine models, as determined by using global transcriptomic profiling. J Allergy Clin Immunol. 2016(19)). As such, it is very difficult to expect the success of clinical trials on the basis of the results of nonclinical trials using an animal model especially in the case of atopic dermatitis. Even when meaningful results are obtained from animal experiments, the clinical trials tend to have a very high probability of failure.

Transient receptor potential vanilloid subfamily member 1 (TRPV1) is widely distributed in skin tissues such as keratinocytes, sebocytes, and sensory nerve fibers, all of which are main constituent cells that account for 90% of the epidermis, and thus serves as an integral regulator that plays a main role in in vivo delivery of various external noxious stimuli into neurons. When TRPV1 is activated by various external stimuli, vanilloid-based compounds, thermal stimuli, and acids (pH), it secretes various pro-inflammatory neuropeptides such as substance P (SP) or calcitonin gene-related peptides (CGRPs) from the peripheral termini of capsaicin-sensitive neurons. In this case, the pro-inflammatory neuropeptides play an important role in cellular signaling modulation which mainly causes neurogenic inflammation (e.g., migraine, asthma, inflammatory bowel disease (IBD), various acute/chronic pains, etc.). Therefore, a TRPV1 antagonist is expected to be used as an effective therapeutic agent for various skin diseases (including diseases associated with TRPV1, such as pain, neuropathy, atopic dermatitis, etc.), inflammatory diseases, and the like.

Accordingly, TRPV1 antagonists were developed by various pharmaceutical companies for treating neurogenic pain, and the like, but the development was mostly stopped during clinical trials. Until recently, new drugs did not come into the market. The clinical trials and the stopping of drug development are generally due to the side effects of the TRPV1 antagonists, such as an increase in body temperature in humans when various compounds such as chemotypes are orally administered. As a representative example, an increase in body temperature is caused when TRPV1 is suppressed in a phase 1/2 clinical trial for an AMG 517 compound, and even serious hyperthermia in which the body temperature of approximately 40° C. lasts for a long time occurs.

SUMMARY OF THE DISCLOSURE

The present invention provides an unexpectedly and significantly improved method for treating atopic dermatitis with a composition containing TRPV1 antagonist, Compound of Formula 1.

In an embodiment, the present invention relates to a TRPV1 antagonist-containing composition capable of effectively preventing and/or treating atopic dermatitis, and a method for preventing and/or treating atopic dermatitis using the same with a low or no side effects known to other TRPV1 antagonist.

In another embodiment, the present invention provides a composition for an external use on skin for preventing and/or treating atopic dermatitis, which includes a TRPV1 antagonist, without any side effects such as an increase in body temperature, epidermal atrophy, and the like when the composition is percutaneously applied onto the skin.

The present invention provides a composition for external use on skin, containing which includes a compound represented by Formula 1 as a TRPV1 antagonist together with a pharmaceutically acceptable carrier. The composition for external use on skin according to the present invention may be used to effectively prevent and/or treat atopic dermatitis.

<Formula 1>

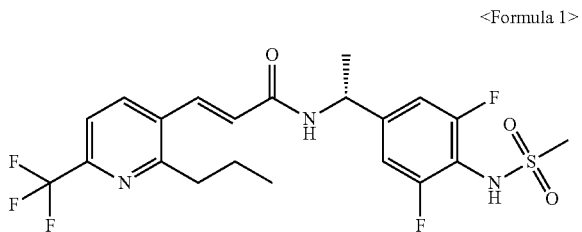 [SMILES: CCCc1nc(C(F)(F)F)ccc1/C=C/C(=O)N[C@H](C)c1cc(F)c(NS(C)(=O)=O)c(F)c1]

The compound of Formula 1 is a material developed as a selective antagonist of TRPV1 by the present inventors, and is disclosed in WO 2008/013414.

It is another embodiment, the present invention provides a method of preventing or treating atopic dermatitis, which includes applying an effective amount of the composition for external use on skin onto the skin of a mammal, including a human.

It is still another object of the present invention to provide a composition for preventing and/or treating atopic dermatitis without any side effects such as an increase in body temperature, epidermal atrophy, and the like.

The method for preventing or treating atopic dermatitis using the compound of Formula 1 according to the present invention may be particularly useful in very effectively and safely preventing or treating atopic dermatitis without an increase in body temperature.

BRIEF DESCRIPTION OF THE DRAWINGS

FIGS. 1A and 1B show the results of nonclinical trials (in vivo) on the change in body temperature at the time of transdermal administration according to Experimental Example 1: FIG. 1A is the results of the change in body temperature at the time of transdermal administration of the AMG 517 compound (Amgen) as a TRPV1 antagonist, and FIG. 1B is a graph showing the results of the change in body temperature at the time of transdermal administration of the compound of Formula 1.

FIGS. 2A and 2B show the results of nonclinical trials (in vivo) on the change in body temperature at the time of oral administration according to Experimental Example 1: FIG. 2A is the results of the change in body temperature at the time of oral administration of the AMG 517 compound (Amgen) as a TRPV1 antagonist, and FIG. 2B is a graph showing the results of the change in body temperature at the time of oral administration of the compound of Formula 1.

FIGS. 3A, 3B, 3C and 3D show the results of a applying experiment of the composition for external use on the skin: FIGS. 3A, 3B and 3C are graphs showing the change rate of the Eczema Area and Severity Index (EASI) score before and after applying the compositions for external use on the skin of Example 1 and Comparative Example 1 (3A: Phase 2 pediatric clinical trials, 3B: Phase 2 adult clinical trials, 3C: Phase 3 clinical trials), and FIG. 3D is a graph showing the change in the EASI score with time after the application (3D: Phase 2 adult clinical trials).

FIGS. 4A, 4B and 4C are graphs showing the improvement of more than 50% (EASI-50), 75% (EASI-75), 90% (EASI-90) of the EASI score before and after the administration of the compositions of Example 1 and Comparative Example 1 (4A: Phase 2 pediatric clinical trials, 4B: Phase 2 adult clinical trials, 4C: Phase 3 clinical trials).

FIGS. 5A and 5B are graphs showing the results of the clinical trials on the Mean changes from baseline in Pruritus VAS before and after applying the compositions of Example 1 and Comparative Example 1, and FIG. 5C is a graph showing the Mean changes from baseline in Pruritus severity score before and after applying the compositions of Example 1 and Comparative Example 1 (5A: Phase 2 adult clinical trials, 5B: Phase 3 clinical trials, 5C: Phase 2 adult clinical trials).

FIGS. 6A and 6B show the results of clinical trials on the changes in body temperature in orally administrating according to Experimental Example 1: FIG. 6A is a graph showing the mean body temperature when the compound of Formula 1 is orally administered, and FIG. 6B is a graph showing the mean change of body temperature when the compound of Formula 1 is orally administered.

FIG. 7 is a graph illustrating the results of comparison experiments between degrees of side effects (e.g., atrophoderma) of steroid drugs and the composition of Example 1; and FIG. 8 is a graph for comparative analysis of therapeutic side effects for atopic dermatitis by measuring a content of moisture in the skin after administration of the steroid drugs and the composition of Example 1.

FIGS. 9A and 9B are the results of an experiment on the change of symptoms of atopic dermatitis when the dosage form of the composition for preventing or treating atopic dermatitis according to the present invention is changed: FIGS. 9A and 9B are graphs showing the degree of atopic symptoms in the case of an ethanol vehicle and a cream vehicle, respectively.

FIGS. 10A and 10B are the results of an experiment on the change in the amount of IgE antibody expression when the dosage form of the composition for preventing or treating atopic dermatitis according to the present invention is changed: FIGS. 10A and 10B are graphs showing the change in the amount of IgE antibody expression in the case of an ethanol vehicle and a cream vehicle, respectively.

DETAILED DESCRIPTION

Hereinafter reference will now be made in detail to various embodiments of the present invention, examples of which are illustrated in the accompanying drawings and described below.

While the invention will be described in conjunction with exemplary embodiments, it will be understood that present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

The term "atopic dermatitis (AD)" used in the present invention refers to a chronic and recurrent eczematous disease that starts in infancy and is accompanied by pruritus, that is, a disease that shows a distinctive distribution and pattern of eruptions depending on the age. Atopic dermatitis is one of the most common skin diseases, especially in infants and young children. It begins at least 45% during 6 months, at least 60% before 12 months, and at least 85% before 5 years of age. In particular, it is known that the prevalence rate of atopic dermatitis is 17.2% in American children, 15.6% in European children and 24% in children aged 5 to 6 in Japan. According to research of the Korean Academy of Pediatric Allergy and Respiratory Disease in 2000, the prevalence rate in Korea was 24% in elementary school students and 13% in middle school students. Recently, atopic dermatitis has been steadily increasing worldwide. As mentioned above, the prevalence rate is 10 to 20% in children and 1 to 3% in adults, which is very similar to the prevalence rate in Korea.

Pruritus is most common in the distinctive symptoms of atopic dermatitis, and acute skin eruptions occur in the form of erythematous papules and blisters together with severe pruritus. In this case, when the eruptions are scratched, oozing lesions may occur, which lead to secondary infection. For the symptoms according to the clinical stages of atopic dermatitis, excoriation, erythematous or scaly papules, and plaque occur in the subacute stage, and lichenification, in which the skin becomes thick when the skin is repeated scratched, occurs in the chronic stage, and prurigo nodularis may be observed even in this stage. Particularly, the skin disease conditions in such various stages may be repeatedly observed at the same time in patients with chronic atopic dermatitis. In all the stages, the patients have a dry and dull skin condition and a frequent relapse of AD and exhibit a chronic disease pattern. Persistent pruritus results in mechanically damaged skin and accelerates various inflammatory responses, thereby keeping up the itch-scratch-itch cycle in which pruritus is induced again.

Also, because the clinical features of atopic dermatitis vary widely and there are currently no specific examination findings of atopic dermatitis, atopic dermatitis is diagnosed by putting the various clinical features together. Representative criteria internationally used are 'Haniffin & Rajka criteria,' which consist of four major criteria such as pruritus, typical morphology and distribution of eruptions, chronic or chronically relapsing dermatitis, and personal or family history of atopic dermatitis, and the other 26 minor criteria such as xerosis, elevated serum IgE, and the like. When there are at least three of the major criteria findings and at least three of the minor criteria findings, atopic dermatitis may be diagnosed. The Haniffin & Rajka criteria are as listed in the following Table 1 (Acta Dermato 1980; 92:44-47).

TABLE 1

Hanifin and Rajka criteria

| Criteria | Findings |
|---|---|
| Major criteria | Pruritus |
| | Typical morphology and distribution of eruptions |
| | Flexural lichenification or linearity in adults, Facial and extensor involvement in infants and children |
| | Chronic or chronically relapsing dermatitis |
| | Personal or family history of atopy (asthma, allergic rhinitis, atopic dermatitis) |
| Minor criteria | Xerosis |
| | Ichthyosis, palmar hyperlinearity, and keratosis pilaris |
| | Immediate (type1) skin test reactivity |
| | Elevated serum IgE |
| | Early age of onset |

TABLE 1-continued

Hanifin and Rajka criteria

| Criteria | Findings |
|---|---|
| | Tendency towards cutaneous infections |
| | Tendency towards non-specific hand or foot dermatitis |
| | Nipple eczema |
| | Cheilitis |
| | Recurrent conjunctivitis |
| | Dennie-Morgan infraorbital fold |
| | Keratoconus |
| | Anterior subcapsular cataracts |
| | Dermatitis of lids and orbital darkening |
| | Facial pallor/facial erythema |
| | Pityriasis alba |
| | Anterior neck folds |
| | Itch when sweating |
| | Intolerance to wool and lipid solvents |
| | Perifollicular accentuation |
| | Food intolerance |
| | Course influenced by environmental/emotional factors |
| | White dermographism/delayed blanch |

The present invention relates to a composition for preventing or treating atopic dermatitis, which includes a compound represented by the following Formula 1, preferably a composition for external use on skin which is percutaneously applied on the skin.

<Formula 1>

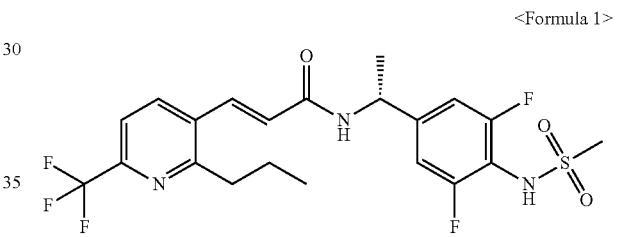

The compound represented by Formula 1 is a TRPV1 (or vanilloid receptor-1) antagonist that is useful in treating pain, neuropathy, various chronic diseases (including atopic dermatitis, and the like), inflammatory skin diseases, and the like. The compound of Formula 1 according to the present invention, the method of preparing the same, and the vanilloid receptor antagonist activity are specifically disclosed in International Publication No. WO 2008/013414, the disclosure of which is incorporated herein by reference in its entirety.

Particularly, the compound of Formula 1 inhibits excessive activity of TRPV1, which is expressed in peripheral nerve fibers and corneocytes distributed in the skin, to prevent the neuropeptide release and calcium influx. In this way, it is found that the compound of Formula 1 may effectively prevent pruritus, inflammation and skin barrier damage to prevent and/or treat atopic dermatitis.

The chemical name of the compound of Formula 1 is (R)-N-[1-(3,5-difluoro-4-methanesulfonylam ino-phenyl)-ethyl]-3-(2-propyl-6-trifluoromethyl-pyridin-3-yl)-acrylamide.

In the present invention, the compound of Formula 1 includes both a parent compound and a pharmaceutically acceptable salt thereof. Examples of the compound of Formula 1 include (1) acid addition salts formed of inorganic acids or formed of organic acids; or (2) salts formed when acidic protons present in the parent compound is replaced.

As an active ingredient of the composition for external use on the skin according to the present invention, the compound represented by Formula 1 may be included in an amount of 0.1 wt. % or more, 0.5 wt. % or more, 0.8 wt. % or more, and 1.5 wt. % or less, 1.2 wt. % or less, based on the total weight of the composition. When the content of the compound represented by Formula 1 falls within this content range, the maximum prophylactic and/or therapeutic effects on atopic dermatitis may be achieved.

The composition for external use on skin according to the present invention is directly applied onto the skin, and has an activator effect in preventing or treating atopic dermatitis without any TRPV1 target-specific side effects such as an increase in body temperature.

Also, the present invention relates to a method of treating, relieving, improving or preventing atopic dermatitis, which includes applying the composition, which included the compound of Formula 1 as the active ingredient, onto the skin of a mammal including a human. Preferably, the composition is a composition for external use on skin capable of effectively preventing and/or treating atopic dermatitis without any side effects such as an increase in body temperature.

The composition of the present invention may be administered to a patient with mild, moderate or severe atopic dermatitis (AD), preferably administered to a patient with mild or moderate atopic dermatitis. According to one exemplary embodiment, the patient is a patient with moderate atopic dermatitis.

Generally, atopic dermatitis can be categorized into mild, moderate, and severe depending on the degrees of symptoms of atopic dermatitis. Specifically, the degrees of symptoms of atopic dermatitis may be divided on the basis of the investigator's global assessment (IGA) grades and the eczema area and severity index (EASI) scores.

IGA is a scale used to diagnose the severity of atopic dermatitis and a clinical response to therapy on the basis of a 6-point scale spanning from 0 (clear symptoms) to 5 (very severe symptoms). In this case, the specific grading criteria are as listed in the following Table 2 (J Am Acad Dermatol 2002; 46: 495-504).

TABLE 2

| Grade | | Details of symptoms |
|---|---|---|
| 0 | Clear symptoms | No inflammatory signs of atopic dermatitis |
| 1 | Almost clear symptoms | Just perceptible erythema, and just perceptible papulation/infiltration |
| 2 | Mild symptoms | Mild erythema, and mild papulation/infiltration |
| 3 | Moderate symptoms | Moderate erythema, and moderate papulation/infiltration |
| 4 | Severe symptoms | Severe erythema, and severe papulation/infiltration |
| 5 | Very Severe symptoms | Severe erythema, and severe papulation/infiltration with oozing/crusting |

Referring to Table 2 above, the subjects to which the composition for external use on the skin of the present invention is to be administered may have IGA grade of 1 or more, 2 or more, and 4 or less, 3 or less. In this case, the composition for external use on skin according to the present invention may have an excellent effect of preventing and/or treating atopic dermatitis without any side effects.

An eczema area and severity index (EASI) is an index for objectively expressing the severity of atopic dermatitis, that is, a verified scale used under clinical environments. The EASI scores are evaluated as points 0 to 6 depending on the area of eruptions of atopic dermatitis in four body parts such as a head/neck, upper limbs, a trunk, and lower limbs, and degrees of symptoms such as erythema, induration/papulation, excoriation, and lichenification are observed, and rated as grades 0 to 3 (grade 0: clear, grade 1: mild, grade 2: moderate, and grade 3: severe) depending on the severity of the symptoms. Thereafter, the EASI score may be obtained by multiplying area scores in the individual body parts by this clinical finding score and summing up all values to calculate the total score. In this case, the area scores of the eruptions of atopic dermatitis are divided on the criteria as listed in the following Table 3, and the calculation formula of the EASI scores is as described in the following Table 4 (*Exp. Dermatol* 2001; 10: 11-18).

TABLE 3

Area scores of eruptions of atopic dermatitis (Area of involvement at 7-point ordinal scale)

| Scales | Details |
|---|---|
| 0 | No eruptions |
| 1 | <10% |
| 2 | 10% to 29% |
| 3 | 30% to 49% |
| 4 | 50% to 69% |
| 5 | 70% to 89% |
| 6 | 90% to 100% |

TABLE 4

EASI score calculation formula (Severity and Area Formulae)

| Body part | calculation formula |
|---|---|
| Head/Neck | (E + I + Ex + L) × Area involvement × 0.1 |
| Upper limbs | (E + I + Ex + L) × Area involvement × 0.2 |
| Trunk | (E + I + Ex + L) × Area involvement × 0.3 |
| Lower limbs | (E + I + Ex + L) × Area involvement × 0.4 |

EASI = the sum of area scores for the fours body parts
E = Erythema
I = Induration/Papulation
Ex = Excoriation
L = Lichenification
Area involvement: area score of eruptions of atopic dermatitis Referring to Table 4, the preferred subjects to which the composition for external use on the skin of the present invention is to be administered may be patients generally having IGA grade of 1 or more, 2(mild) or more, and 4 or less, 3(moderate) or less, or EASI score of 0.1 or more, 1.1 or more, 50 or less, 21 or less (British Journal of Dermatology 2015; 172: 1353-1357). In this case, the composition for external use on skin according to the present invention may have an excellent effect of preventing and/or treating atopic dermatitis without any side effects.

Further, the subjects to which the composition for external use on the skin of the present invention is to be administered may be patients suffering from the atopic dermatitis with eruption sites having a body surface area (BSA) of 1% or more, 5% or more, and 100% or less, 30% or less. In this case, the BSA is a value obtained by calculating an area of eruption sites with respect to the total area (100%) of the skin according to the rule of 9's.

Further, the subjects to which the composition for external use on skin according to the present invention is to be administered may be patients with moderate or more severe atopic dermatitis who are resistant to or unreactive with topical corticosteroid drugs (TCSs) or do not sufficiently react with the TCSs.

Generally, because the patients with moderate or more severe atopic dermatitis often receive therapy using the topical corticosteroid drugs, the patients with moderate atopic dermatitis may be resistant to or unreactive with the topical corticosteroid drugs.

Therefore, the composition for external use on skin may have an excellent therapeutic effect in the patients with moderate atopic dermatitis, that is, patients having an EASI of 6.1 (or 7.1) to 50 or an EASI of 6.1 (or 7.1) to 21, the value of which generally corresponds to an IGA score of 3 to 4 or an IGA score of 3 (moderate) according to the typical criteria as described above, or even the patients who are resistant to or unreactive with the topical corticosteroid drugs or do not sufficiently react with the topical corticosteroid drugs.

Further, the subjects to which the composition for external use on the skin of the present invention is to be administered may be selected from children, adolescents and adults.

On the basis of age, the children may be at least 24 months, less than 12 years old, the adolescents may be at least 12 years old, less than 19 years old, and the adults may be at least 19 years old, at most 70 years old.

The composition for external use on skin according to the present invention is percutaneous applied. In this case, the composition may be applied twice a day until the eruptions improve, preferably may be applied for 8 weeks.

Also, a single dose of the composition for external use on skin varies depending on the condition and weight of a patient, the severity of a disease, the type of a composition, a route of administration, and the administration duration. In this case, the dose of the composition applied refers to an amount (i.e., a finger-tip unit (FTU); 0.5 g) of a cream that is squeezed in a row to a length of the last knuckle of the patient's index finger, that is, a proper amount of the cream that is once applied to an area (i.e., approximately 2% body surface area (BSA)) which is twice the size of the patient's palm. In the case of a patient with eruptions of 5% to 30% BSA, the composition for external use may be preferably administered at a dose of 10 mg to 300 mg in consideration of the severity of the patient with atopic dermatitis, and the administration method as described above, may, for example, be properly adjusted and administered in a range of the daily dose in consideration of the size and shape of a lesion, the severity of symptoms, the age of a patient, and the like. In addition, the daily dose may be 5 mg or more, 10 mg or more, 12.5 mg or more, 20 mg or more, 25 mg or more, and 200 mg or less, 175 mg or less, 150 mg or less, 100 mg or less, 87.5 mg or less, but is not limited therein.

The composition for external use on skin according to the present invention may improve the following parameters (a) to (d) associated with atopic dermatitis:

(a) improving an IGA grade of 2 for a patient (with mild symptoms) to grade 1 (almost clear symptoms) or 0 (clear symptoms);

(b) improving an IGA grade of 3 for a patient (with moderate symptoms) to grade 2 (mild symptoms), grade 1 (almost clear symptoms), or grade 0 (clear symptoms) or grade 1 (almost clear symptoms) or 0 (clear symptoms);

(c) improving an EASI score and reducing the EASI score by at least 40% or more; and (d) reducing a VAS or a pruritus index represented by pruritus severity.

The definitions of IGA and EASI and the rating method are as described above.

In particular, in pediatric patients, the EASI score may be reduced by at least 60%, or at least 75% from baseline.

Further, in adult patients, the EASI score may be reduced by at least 50%, or at least 75% from baseline.

The composition for external use on skin according to the present invention may be particularly prepared into a cream, a gel, a patch, a spray, an ointment, a plaster, a lotion, a liniment, a paste, a cataplasma, a serum, a pack, a powder, an oil, a wax, a spray, a paste, a solution, a suspension, an emulsion, or a soap.

Meanwhile, the composition may further include various known components in a range which does not hinder the effect of the compound represented by Formula 1, depending on desired formulations. According to one exemplary embodiment, the composition may further include additives selected from the group consisting of a carrier, an emulsifying agent, a moisturizing agent, a skin conditioning agent, a surfactant, a chelating agent, an antioxidant, a disinfectant, a stabilizing agent, and any combination thereof.

The carrier may include animal fibers, vegetable fibers, wax, paraffin, starch, tragacanth, cellulose derivatives, polyethylene glycol, silicone, bentonite, silica, talc, zinc oxide, lactose, silica, aluminum hydroxide, calcium silicate, polyamide powder, water, ethanol, isopropanol, ethyl carbonate, ethyl acetate, benzyl alcohol, benzyl benzoate, propylene glycol, 1,3 butylene glycol, glycerol aliphatic ester, polyethylene glycol, liquid diluents, ethoxylated isostearyl alcohol, suspending agents such as polyoxyethylene sorbitol ester and polyoxyethylene sorbitan ester, microcrystalline cellulose, aluminum metahydroxide, bentonite, agar or tragacanth, aliphatic alcohol sulfate, aliphatic alcohol ether sulfate, sulfosuccinate monoester, isethionate, imidazolinium derivatives, methyl taurate, sarcosinate, fatty acid amide ether sulfate, alkyl amido betaine, aliphatic alcohol, fatty acid triglyceride, fatty acid diethanol amide, vegetable oil, linolic acid derivatives, or ethoxylated glycerol fatty acid ester, but the present invention is not limited thereto.

The moisturizing agent may include glycerin, glyceryl stearate, and the like, but the present invention is not limited thereto.

The skin conditioning agent may include cyclomethicone, dimethicone, and the like, but the present invention is not limited thereto.

The surfactant may include polyoxyethylene-sorbitan-fatty acid esters, polyoxyethylene fatty acid esters, sorbitan fatty acid esters, polyoxyethylene-polyoxypropylene copolymers, cetearyl glucoside, and mono-/di-glycerides, but the present invention is not limited thereto.

The chelating agent may include ethylenediaminetetraacetic acid (EDTA), α-hydroxy fatty acid, lactoferrin, α-hydroxy acid, citric acid, lactic acid, malic acid, bilirubin, biliverdin, and the like, but the present invention is not limited thereto.

The antioxidant may include butylhydroxyanisole, dibutyl hydroxy toluene, or propyl gallate, but the present invention is not limited thereto.

In addition, components that may be mixed in the composition for external use on skin may include a pH control agent, a plasticizing agent, a solubilizing agent, a gelling agent, a binder, an isotonic agent, a soothing agent, a preservative, a dispersing agent, an opacifying agent, an antioxidant, an osmoregulatory agent, an antifoaming agent, a wetting agent, a thickening agent, an adhesive, a masking agent, a coloring agent, a flavoring agent, a film-forming agent, a suspending agent, a volatile restrainer, an absorbent, an oily component, an emollient, an organic and inorganic pigment, an organic powder, a UV absorbent, an alcohol, a blood flow stimulant, a cooling agent, a limiting agent, and the like.

The composition for external use on skin according to the present invention may be preferably in the form of an oil-in-water (O/W) emulsion, which includes:

(1) the compound of Formula 1 as a drug;

(2) one or more components selected from the group consisting of a cellulose-based polymer and a vinylpyrrolidone-based polymer as the stabilizing agent;

(3) one or more components selected from the group consisting of diethylene glycol monoethylether, polyethylene glycol, 2-pyrrolidone, and dimethyl sulfoxide as a solvent;

(4) water as an aqueous component;

(5) one or more components selected from the group consisting of PEG-30 hydrogenated castor oil, medium-chain triglyceride, cetostearyl alcohol, squalane and cyclomethicone as an oily component;

(6) one or more components selected from the group consisting of a polyoxyethylene-sorbitan-fatty acid ester, a polyoxyethylene fatty acid ester, a sorbitan fatty acid ester, a polyoxyethylene-polyoxypropylene copolymer, a cetearyl glucoside, and a mono-/di-glyceride as the surfactant; and (7) one or more components selected from the group consisting of xanthan gum, gelatin, gellan gum, carragheenan, and carbomer as the thickening agent.

In the composition of the present invention, the compound of Formula 1 as the drug may be included at a content of 0.1 to 1.5% by weight, based on the total weight of the composition. The cellulose-based polymer or vinylpyrrolidone-based polymer as the stabilizing agent may be included at a content of 1 to 5% by weight, based on the total weight of the composition. The solvent may be included at a content of 5 to 20% by weight, based on the total weight of the composition. The aqueous component may be included at a content of 45 to 90% by weight, based on the total weight of the composition. The oily component may be included at a content of 5 to 30% by weight, the surfactant may be included at a content of 1 to 10% by weight, and the thickening agent may be included at a content of 0.01 to 5% by weight, based on the total weight of the composition.

Therefore, as described above, when the composition is administered twice a day for 4 weeks to 25 male and female patients, aged 24 months to less than 12 years old, who have been diagnosed with mild and moderate atopic dermatitis so that the composition is applied onto the skin as described below, in Phase 2 pediatric clinical trials, the composition has an excellent therapeutic success rate of approximately 61% in the optimal dose test group, compared to the placebo group (see Experimental Example 2). Also, the change rate in body temperature of the test group receiving a test drug in the course of treatment showed a lower rate of body temperature rise of 0.04° C. than the placebo group.

Further, when the composition is administered twice a day for 8 weeks to 97 male and female patients, aged 19 to 70 years old, who have been diagnosed with mild and moderate atopic dermatitis so that the composition is applied onto the skin, in Phase 2 adult clinical trials, the composition has an excellent therapeutic success rate of approximately 60% in the optimal dose test group, compared to the placebo group (see Experimental Example 2). Also, the change rate in body temperature of the test group receiving a test drug in the course of treatment showed a lower rate of body temperature rise of 0.02° C. than the placebo group.

Further, in Phase 3 clinical trials as a therapeutic confirmatory clinical trial, the test was conducted twice a day for 8 weeks to 240 adolescents and male and female adults, aged 12 to 70 years old, who have been diagnosed with mild to moderate atopic dermatitis. As a result, it was confirmed that the therapeutic success rate was 35.95% (see Experimental Example 2). Also, the change rate in body temperature of the test group receiving a test drug in the course of treatment showed a lower rate of body temperature rise of –0.01° C. than the placebo.

From these results, it can be seen that the composition for external use on the skin of the present invention including the compound of Formula 1 as the active ingredient may be used to effectively treat mild or moderate atopic dermatitis in children, adolescents and male and female adult patients aged 24 months to 70 years old without causing any side effects such as an increase in body temperature when percutaneously applied on the skin.

Example 1: Preparation of Composition for External Use on Skin Including Compound of Formula 1

A composition for external use on skin in the form of a cream formulation including the compound of Formula 1 was prepared using the components and contents as listed in the following Table 5. Specifically, the oily and aqueous components having the contents as listed in the following Table 5 were first emulsified at 65° C., and a solution of the compound of Formula 1 dissolved in polyethylene glycol (PEG400 commercially available from Merck) which was the base was then added thereto. Thereafter, a thickening agent and additives were added thereto, homogenized, and then cooled to 35° C. to prepare a composition for external use on skin in the form of a cream formulation.

Comparative Example 1: Preparation of Placebo Composition (Including No Compound of Formula 1) for Comparison with Example 1

A composition for external use on skin in the form of a cream formulation was prepared in the same manner as in Example 1 using the same components and contents as listed in the following Table 5, except that the compound of Formula 1 was not used.

TABLE 5

| Units: % by weight | Components | Example 1 | Comparative Example 1 |
|---|---|---|---|
| Oily components | Medium-chain triglyceride | 4.5 | 4.5 |
| | Cetostearyl alcohol | 3.5 | 3.5 |
| | Cyclomethicone | 4.5 | 4.5 |
| Surfactants | Polysorbate 60 | 1.5 | 1.5 |
| | Mono-/di-glyceride | 1.5 | 1.5 |
| Thickening agent | Carbomer | 0.25 | 0.25 |
| Active ingredient | Compound of Formula 1 | 1 | 0 |
| Aqueous component | Purified water | Balance | Balance |
| Base | PEG 400 | 10 | 10 |
| Stabilizing agent | Hypromellose 2910 | 2.5 | 2.5 |
| Additives | Preservative, Neutralizing agent, Pigment, and Flavoring agent | Proper amounts | Proper amounts |

Formulation Example 1: Gel

A gel including the compound of Formula 1 according to the present invention was prepared according to a conventional method using the components and contents as listed in the following Table 6.

TABLE 6

| Components | % by weight |
| --- | --- |
| Compound of Formula 1 | 1 |
| PEG 400 | 10 |
| Hypromellose 2910 | 2 |
| α-ketoglutaric acid | 1.0 |
| Niacinamide | 1.0 |
| β-1,3-glucan | 0.1 |
| Ethylenediamine sodium acetate | 0.05 |
| Glycerin | 5.0 |
| Carboxyvinylpolymer | 0.3 |
| Ethanol | 5.0 |
| Triethanolamine | 0.3 |
| Preservative and Flavoring agent | 0.1 |
| Purified water | Balance |

Formulation Example 2: Ointment

An ointment including the compound of Formula 1 according to the present invention was prepared according to a conventional method using the components and contents as listed in the following Table 7.

TABLE 7

| Components | % by weight |
| --- | --- |
| Compound of Formula 1 | 1 |
| PEG 400 | 10 |
| Hypromellose 2910 | 2.5 |
| α-ketoglutaric acid | 1.0 |
| Niacinamide | 1.0 |
| β-1,3-glucan | 10.0 |
| Wax | 10.0 |
| Polysorbate | 5.0 |
| PEG-60 hydrogenated castor oil | 2.0 |
| Sorbitan sesquioleate | 0.5 |
| Vaseline | 5.0 |
| Liquid paraffin | 10.0 |
| Squalane | 5.0 |
| Shea butter | 3.0 |
| Caprylic/capric triglyceride | 5.0 |
| Glycerin | 10.0 |
| Propylene glycol | 10.2 |
| Triethanolamine | 0.2 |
| Preservative and Flavoring agent | 0.1 |
| Purified water | Balance |

Formulation Example 3: Lotion

A lotion including the compound of Formula 1 according to the present invention was prepared according to a conventional method using the components and contents as listed in the following Table 8.

TABLE 8

| Components | % by weight |
| --- | --- |
| Compound of Formula 1 | 1 |
| PEG 400 | 10 |
| Hypromellose 2910 | 2 |
| Shea butter | 3.0 |
| Caprylic/capric triglyceride | 5.0 |
| Polysorbate | 3.0 |
| Glycerin | 10.0 |
| Propylene glycol | 10.2 |
| Triethanolamine | 0.2 |
| Preservative and Flavoring agent | 0.1 |
| Purified water | Balance |

Experimental Example 1: Comparison of Changes in Body Temperature in Nonclinical Trials (In Vivo) by Administration of TRPV1 Antagonist Development of the AMG 517 compound represented by the following Formula 2 as a representative TRPV1 antagonist was discontinued, due to the side effects associated with body temperature during clinical trials for the treatment of toothache by Amgen, a multinational pharmaceutical company. According to Amgen's announcement, it was confirmed that the body temperature is increased by about 1.3° C. in rats at the oral dose of 3 mg/kg, and it is considered that the effective concentration to maximize analgesic efficacy was less than 0.3 mg/kg in rats, and this dose did not significantly raise the issue of side effects and thus clinical trials were proceeded. It was confirmed that oral administration for the treatment of dental pain has been reported to raise body temperature in human up to about 40° C. and resulted in a concentration-dependent side effect of hyperthermia (Gavva et al., 2008. Pain 136, 202-210):

<Formula 2>

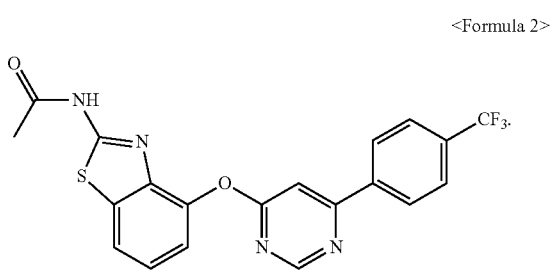 [SMILES: CC(=O)Nc1nc2c(Oc3cc(-c4ccc(C(F)(F)F)cc4)ncn3)cccc2s1]

As described above, AMG 517, a representative reference drug as a TRPV1 antagonist, and the compound of Formula 1 of the present invention were tested for the increase in body temperature during transdermal administration. Considering the different drug absorption patterns due to damage to the skin barrier in patients with skin diseases such as atopic dermatitis, after damaging the keratin by tape stripping the skin of the back of experimental animals (C57BL/6 mice), the changes in body temperature were observed at 0, 1, 2, 4, and 6 hours before and after transdermal application with 0.1%, 0.3%, and 1.0% test materials. In this case, as shown in FIG. 1A, it is confirmed that when AMG 517 was applied, a significant concentration-dependent increase in body temperature (~1.59° C.) was observed at 2 hours after administration of all concentrations, as compared with before application. As shown in FIG. 1B, when the compound of Formula 1 was applied, body temperature in the 1.0% dose group was increased only by 2 hours (~0.84° C.) but no concentration dependence was observed.

Meanwhile, when the same drug was orally administered, a concentration-dependent increase in body temperature due to TRPV1 antagonism was observed as expected (see FIGS. 2A and 2B). Specifically, the changes in body temperature of up to 4 hours by administration of 0.03, 0.1 and 0.3 mg/kg of AMG 517 (FIG. 2A), and 3, 10 and 30 mg/kg of compound of Formula 1 (FIG. 2B) were observed in experimental animals (Balb/c mice). Both drugs increased body temperature in a dose-dependent manner, and AMG 517 significantly increased body temperature at a very low dose of 0.03 mg/kg.

Experimental Example 2: Clinical Drug Administration According to Types of Composition for External Use on Skin Clinical trials were performed to evaluate safety and efficacy of the compositions for external use on skin prepared in Example 1 and Comparative Example 1.

The clinical trials were conducted as Phase 2 clinical trials and Phase 3 clinical trials for patients diagnosed with atopic dermatitis. Generally, Phase 2 clinical trials are trials for evaluating the efficacy and safety of test drugs in patients to determine the potential as new drugs, optimal dose and use, and to explore therapeutic effects. Phase 3 clinical trials are the largest clinical trials to obtain additional information and corroborating data on the effectiveness of the drugs.

Hereinafter, Phase 2 clinical trials and Phase 3 clinical trials will be described in detail. Subjects to which the drug will be administered for the Phase 2 clinical trials were divided into children and adults, which are referred to as Phase 2 pediatric clinical trials and Phase 2 adult clinical trials.

The experimental groups administered with the compositions for external use on the skin of Example 1 and Comparative Example 1 correspond to the test group (PAC-14028 cream 1.0%) and the placebo group (vehicle cream), respectively.

(1) Phase 2 Pediatric Clinical Trials

Subjects to which the composition was to be administered were male and female children patients, aged 24 months to less than 12 years old, who have been diagnosed with atopic dermatitis based on the Hanifin and Rajka diagnostic criteria. The patients having eruptions due to mild and moderate atopic dermatitis, which corresponded to an IGA grade of 2 to 3, were subjected to randomized, double-blind, multicenter, and placebo-controlled parallel-design trials.

Specifically, the subjects to which the compositions for external use on the skin of Example 1 and Comparative Example 1 were applied were divided into groups of 13 patients (test group, n=13) and 12 patients (placebo group, n=12) who suffered from atopic dermatitis. The clinical trials were conducted in 24 months to less than 12 year-old male and female patients who had been diagnosed with mild and moderate atopic dermatitis and who had eruption sites having a body surface area (BSA) of 5% or more and an investigator's global assessment (IGA) grade of 2 to 3.

A method of administration was performed by percutaneously applying the composition for external use on the skin twice a day for 4 weeks. In the children group, aged 24 months to less than 12 years old, the composition was applied onto the skin so that the daily dose of the composition was in a range of approximately 12.5 to 87.5 mg/day, and in the children group, aged 6 years to less than 12 years old, the composition was applied so that the daily dose of the composition was in a range of approximately 25 to 175 mg/day.

(2) Phase 2 Adult Clinical Trials

Subjects to which the composition was to be administered were male and female adult patients, aged 19 years to 70 years old, who have been diagnosed with atopic dermatitis based on the Hanifin and Rajka diagnostic criteria. The patients having eruptions due to mild and moderate atopic dermatitis, which corresponded to an IGA grade of 2 to 3, were subjected to randomized, double-blind, multicenter, and placebo-controlled parallel-design trials.

Specifically, the subjects to which the compositions for external use on the skin of Example 1 and Comparative Example 1 were applied were divided into groups of 48 patients (test group, n=48) and 49 patients (placebo group, n=49) who suffered from atopic dermatitis. The clinical trials were conducted in 19 to 70 year-old male and female patients who had been diagnosed with mild and moderate atopic dermatitis and who had eruption sites having a body surface area (BSA) of 5% or more and an investigator's global assessment (IGA) grade of 2 to 3.

A method of administration was performed by percutaneously applying the composition for external use on the skin twice a day for 8 weeks. The composition was applied onto the skin so that the daily dose of the composition was in a range of approximately 25 to 250 mg/day.

(3) Phase 3 Clinical Trials

Subjects to which the composition was to be administered were male and female adolescent and adult patients, aged 12 years to 70 years old, who have been diagnosed with atopic dermatitis based on the Hanifin and Rajka diagnostic criteria. The patients having eruptions due to mild and moderate atopic dermatitis, which corresponded to total BSA of 5% to 30% and an IGA grade of 2 (mild) or 3 (moderate), were subjected to randomized, double-blind, multicenter, and placebo-controlled parallel-design trials.

Specifically, the subjects to which the compositions for external use on the skin of Example 1and Comparative Example 1 were applied were divided into groups of 160 patients (test group, n=160) and 80 patients (placebo group, n=80) who suffered from atopic dermatitis.

Data of the patients were excluded, who did not participate to the end of the Phase 3 clinical trials due to contact disruptions or violated clinical protocols using other drugs. Therefore, the results of phase 3 clinical trials of the following Experimental Examples 2-1 to 2-4 are the results for the test groups (n=153) and the placebo groups (n=78) except the above patients.

A method of administration was performed by percutaneously applying the composition for external use on the skin twice a day for 8 weeks. The composition was applied onto the skin so that the daily dose of the composition was in a range of approximately 25 to 150 mg/day.

Experimental Example 2-1: Analysis of Therapeutic Success Rate for Atopic Dermatitis Using IGA In this clinical trial, a therapeutic success rate of the composition for external use on skin to treat atopic dermatitis was analyzed to determine an IGA grade.

In this case, IGA is used to evaluate the severity of atopic dermatitis and a clinical response to therapy on the basis of a 6-point scale spanning from 0 (clear symptoms) to 5 (very severe symptoms).

The IGA grade of 0 to 1 was considered to be a success of therapy, and the IGA grade of 2 to 5 was considered to be a failure of therapy.

TABLE 9

| | Phase 2 pediatric clinical trials | | |
|---|---|---|---|
| Therapeutic success rate (IGA grade) | Example 1 (test group, n = 13) | Comparative Example 1 (placebo group, n = 12) | p-value |
| Success (IGA 0 to 1) | 61.54% | 8.33% | 0.0112 (Comparative Example 1, vs. placebo) |

TABLE 9-continued

| Phase 2 adult clinical trials | | | |
|---|---|---|---|
| Therapeutic success rate (IGA grade) | Example 1 (test group, n = 48) | Comparative Example 1 (placebo group, n = 49) | p-value |
| Success (IGA 0 to 1) | 57.45% | 14.58% | 0.0001 (Comparative Example 1, vs. placebo group) |
| Phase 3 clinical trials | | | |
| Therapeutic success rate (IGA grade) | Example 1 (test group, n = 153) | Comparative Example 1 (placebo group, n = 78) | p-value |
| Success (IGA 0 to 1) | 35.95% | 12.82% | 0.0002 (Comparative Example 1, vs. placebo group) |

Referring the Table 9, it can be seen that the therapeutic success rates for atopic dermatitis at the time point of week 8 after administration of the compositions for external use on the skin of Comparative Example 1 and Example 1 were 8.33% and 61.54% in the Phase 2 pediatric clinical trials, 14.58% and 57.45% in the Phase 2 adult clinical trials, and 12.82% and 35.95% in the Phase 3 clinical trials, respectively, indicating that the composition for external use on the skin of the present invention had a statistically significant and excellent therapeutic effect.

Experimental Example 2-2: Analysis of Therapeutic Success Rate for Atopic Dermatitis Using EASI The EASI was evaluated in patients with atopic dermatitis to analyze the therapeutic success rate of the composition for external use on skin to treat atopic dermatitis.

In this case, the EASI was determined by evaluating the disease features of atopic dermatitis as points 0 to 6 depending on the area of eruptions of atopic dermatitis in four body parts such as a head/neck, upper limbs, a trunk, and lower limbs, and degrees of erythema, induration/papulation, excoriation, and lichenification are observed, and rated as grades 0 (clear) to 3 (severe) depending on the severity of the symptoms. Thereafter, the EASI may be obtained by multiplying area scores in the individual body parts by this clinical finding score and summing up all the values to calculate the total score.

The EASI scores determined before the compositions for external use on skin prepared in Example 1 and Comparative Example 1 were applied and after the compositions were applied for 4-8 weeks were used to calculate a change in the EASI score after the 4-8-week percutaneous application with respect to the EASI score before the percutaneous application. The results are listed in the following Table 10. Also, it can be seen that, when the degrees of improvement of the clinical signs such as erythema, induration/papulation, excoriation, and lichenification were scored as the EASI and compared, the composition for external use on skin prepared in Example 1 has an effect of clinically significantly reducing the clinical signs when administered for 8 weeks (see FIGS. 3A, 3B, 3C and 3D).

TABLE 10

| Phase 2 pediatric clinical trials | | |
|---|---|---|
| Experiments Contents | Example 1 (test group, n = 13) | Comparative Example 1 (placebo group, n = 12) |
| Change in EASI score | −60.25% | −31.17% |
| Phase 2 adult clinical trials | | |
| Experiments Contents | Example 1 (test group, n = 48) | Comparative Example 1 (placebo group, n = 49) |
| Change in EASI score | −51.43% | −39.83% |
| Phase 3 clinical trials | | |
| Experiments Contents | Example 1 (test group, n = 153) | Comparative Example 1 (placebo group, n = 78) |
| Change in EASI score | −44.34% | −21.43% |

As listed in Table 10, it can be clinically seen that the EASI scores of the children, adolescent and adult patients decreased by 60.25% (Phase 2 pediatric clinical trials), 51.4% (Phase 2 adult clinical trials) and 44.34% (Phase 3 clinical trials) from a baseline when the composition for external use on the skin prepared in Example 1 of the present invention was administered, indicating that the composition had an excellent therapeutic effect for atopic dermatitis.

Also, as can be seen in the results of the clinical trials of FIGS. 4A to 4C, the groups of patients who exhibited 75% (EASI-75), or 90% (EASI-90) or more improvements (reductions) of EASI scores before and after administration of the compositions of Example 1 and Comparative Example 1 were compared.

In the Phase 2 pediatric clinical trials, when the composition for external use on the skin of Example 1 of the present invention was administered, the EASI scores were 53.85% (EASI-75) and 15.38% (EASI-90), indicating that the composition had a clinically excellent therapeutic effect, compared to the values of 25.0% (EASI-75) and 0.0% (EASI-90) when the composition of Comparative Example 1 was administered (FIG. 4A).

In the Phase 2 adult clinical trials, when the composition for external use on the skin of Example 1 of the present invention was administered, the EASI scores were 43% (EASI-75) and 21% (EASI-90), indicating that the composition had a clinically excellent therapeutic effect, compared to the values of 25% (EASI-75) and 8% (EASI-90) when the composition of Comparative Example 1 was administered (FIG. 4B).

Also, in the Phase 3 clinical trials, when the composition for external use on the skin of Example 1 of the present invention was administered, the EASI scores were 23.5% (EASI-75) and 9.8% (EASI-90), indicating that the composition had a clinically excellent therapeutic effect, compared to the values of 11.5% (EASI-75) and 2.6% (EASI-90) when the composition of Comparative Example 1 was administered (FIG. 4C).

Experimental Example 2-3: Therapeutic Effect for Atopic Dermatitis by Improvement of Pruritus On weeks 4 (children) and 8 (adolescents and adults) from a baseline after the application of the compositions for external use on the skin, in the Phase 2 children and adults patients and the Phase 3 adolescents and adults patients, degrees of pruritus in which the individual patients felt when the composition was applied were evaluated as a visual analogue scale (VAS) and measured mean change in pruritus VAS.

As a result of the Phase 2 pediatric clinical trials for the Mean changes from baseline in Pruritus VAS before and after the application of the composition, Example 1 showed −47.37%, indicating clinically significant efficacy, compared to −36.67% when Comparative Example 1 was administered.

FIG. 5A is a graph showing the results of the Phase 2 adult clinical trials on Mean changes from baseline in Pruritus VAS before and after the application of the compositions of Example 1 and Comparative Example 1, and FIG. 5B is a graph showing the results of the Phase 3 clinical trials on Mean changes from baseline in Pruritus VAS before and after the application of the compositions of Example 1 and Comparative Example 1.

FIG. 5C is a graph showing the results of the Phase 2 adult clinical trials on Mean changes from baseline in Pruritus severity score before and after the application of the compositions of Example 1 and Comparative Example 1. In this case, the evaluation criteria of the Pruritus severity score are as shown in Table 11 below, and the intensity of the pruritus and scratching behavior during the last 24 hours was directly assessed by the patient on a 4-point scale.

TABLE 11

| Pruritus severity score | | |
|---|---|---|
| Score | Grade | Description |
| 0 | Absent | No pruritus |
| 1 | Mild | Occasional slight pruritus & scratching |
| 2 | Moderate | Constant or intermittent pruritus & scratching, causing no disturbing sleep |
| 3 | Severe | Bothersome pruritus & scratching with the difficulty in daily life, causing disturbing sleep |

As listed in FIGS. 5A, 5B and 5C, it can be seen that the composition of the present invention had an effect of statistically significantly improving pruritus from the first week of drug administration, compared to the placebo composition. Also, after a placebo or a test drug was administered to the patients, the efficacy of a change in pruritus severity scores was evaluated. As a result, it can be seen the composition of the present invention had an effect of significantly improving pruritus, which was similar to that in the VAS evaluation. The pruritus severity scores were measured by allowing the patients to directly evaluate pruritus and scratching intensity for the scores on the 4-point scale for 24 hours after the placebo or test drug was administered to the patients, as listed in the following tables. From the above results, it can be seen that the composition including the compound of Formula 1 of the present invention can be used to effectively treat pruritus, which is a major symptom in patients with atopic dermatitis by percutaneous administration.

Experimental Example 2-4: Comparison of Changes in Body Temperature after Percutaneous Administration Next, the difference in body temperature before application (Baseline) and after 4-week application (children)/8-week application (adolescents/adults)(End of study) of the composition for external use on the skin was used to calculate the change in body temperature of patients with atopic dermatitis, as listed in Table 12 below.

TABLE 12

| Phase 2 pediatric clinical trials | | |
|---|---|---|
| Body temperature (° C.) | Example 1 (n = 13) | Comparative Example 1 (n = 12) |
| Baseline | 36.82 ± 0.25 | 36.66 ± 0.27 |
| End of study | 36.86 ± 0.21 | 36.82 ± 0.16 |
| Change | 0.04 ± 0.19 | 0.16 ± 0.26 |
| Phase 2 adult clinical trials | | |
| Body temperature (° C.) | Example 1 (n = 48) | Comparative Example 1 (n = 49) |
| Baseline | 36.50 ± 0.19 | 36.48 ± 0.19 |
| End of study | 36.51 ± 0.24 | 36.52 ± 0.20 |
| Change | 0.02 ± 0.16 | 0.06 ± 0.14 |
| Phase 3 clinical trials | | |
| Body temperature (° C.) | Example 1 (n = 153) | Comparative Example 1 (n = 78) |
| Baseline | 36.49 ± 0.23 | 36.42 ± 0.22 |
| End of study | 36.48 ± 0.24 | 36.42 ± 0.24 |
| Change | −0.01 ± 0.28 | 0.00 ± 0.24 |

Referring to Table 12, it can be seen that, when the composition of Example 1 of the present invention was percutaneously applied to the subjects to which the composition was to be administered using the administration method, in children of 24 months old to adults of 70 years old, no clinically significant changes in body temperature was observed with respect to elevated body temperature, which is a common side effect of conventional TRPV1 antagonists.

Experimental Example 3: Measurement of Change in Body Temperature in Healthy Volunteers after Percutaneous Administration The composition of Example 1 including the compound of Formula 1 was percutaneously applied to healthy volunteers other than the patients with atopic dermatitis to check a change in body temperature.

The 24 healthy adult volunteers were divided into three groups, and the volunteers in each of the groups were then randomly allocated into a test group of 6 volunteers (Example 1) and a placebo group of 2 volunteers (Comparative Example 1). The same clinician applied the composition onto the volunteers' back skins at a dose of 5, 15, 50 mg per 5 g every morning according to a predetermined administration method. In this case, the composition was applied for 7, 15, 30 days with a size of 25×40 cm and an area of 1,000 cm².

The 24 volunteers who participated in this clinical trial to be asked to apply the compositions prepared in Example 1 and Comparative Example 1 did not have clinically significant findings associated with the changes in body temperature, as measured daily before and after administration of the compositions. A range of the body temperatures measured for the 24 volunteers in a clinical trial period was in a range of 35.4 to 37.3° C. The results of the changes in body temperatures from the baseline before the drug administration in each of the groups are as listed in the following Table 13. In this case, the experimental results showed no specific tendency according to the dose and the administration duration.

TABLE 13

| Dose/administration duration (n) | Example 1 | | | Comparative Example 1 Placebo (n = 6) |
|---|---|---|---|---|
| | 5 mg/ 7 days (n = 6) | 15 mg/ 15 days (n = 6) | 50 mg/ 30 days (n = 6) | |
| Increase in body temperature of 1 to 2° C. | 0 | 0 | 2 | 2 |
| Increase in body temperature of ≥2° C. | 0 | 0 | 0 | 0 |
| Decrease in body temperature of 1 to 2° C. | 0 | 0 | 1 | 0 |
| Decrease in body temperature of ≥2° C. | 0 | 0 | 0 | 0 |

Therefore, it was confirmed that no clinically significant increase in body temperature was observed when the composition of Example 1 of the present invention was applied once a day or twice a day for 1 to 8 weeks to the patients with atopic dermatitis who were judged to have serious skin barrier damage and the healthy volunteers who had skin having no skin barrier damage.

Experimental Example 4: Measurement of Change in Body Temperature in Healthy Volunteers after Oral Administration Ten healthy adult volunteers were divided into two groups, and the compound of Formula 1 was orally administered to the volunteers in each of the groups at a dose of 5 mg or 10 mg once a day for 8 days. Thereafter, a placebo was administered to the two volunteers in each of the groups, and the body temperatures were measured for 14 days. Then, the mean body temperature of the volunteers and a change in body temperature were determined. The results are shown in FIGS. 6A and 6B.

As shown in FIGS. 6A and 6B, it was confirmed that the compound of Formula 1 increased the body temperature in a dose-dependent manner by inhibiting the TRPV1 activity when the compound of Formula 1 was orally administered. As the representative TRPV1 antagonist, AMG 517 which was developed by the multinational pharmaceutical company 'Amgen' and whose development was stopped in the clinical development stage caused the volunteers to have an increased body temperature, which was proportional to a serum AMG 517 concentration in the clinical trials of oral administration for treatment of toothache. Particularly, it was reported that the body temperature increased to 39.9° C. in the group in which the AMG 517 was administered at a dose of 25 mg (Pain 2008; 136: 202-210). The results were similar to the facts that the side effects such as an increased body temperature (hyperthermia) were caused in a concentration-dependent manner when the compound of Formula 1 was orally administered.

Therefore, it was expected that an increase in body temperature would be caused by the TRPV1 antagonism even when the compound of Formula 1 was applied onto the skin. However, it was surprisingly clinically found the present invention that such an increase in body temperature was not observed when the compound of Formula 1 was percutaneously applied, as listed in Table 13.

Experimental Example 5: Comparison of Side Effects Such as Atrophoderma Between Topical Steroid Drug and Composition of Example 1

When the composition of Example 1 was applied onto the skins of patients with atopic dermatitis twice a day for 8 weeks, the clinician's visual findings showed that the specific side effects such as epidermal atrophy were not observed in the skin with eruptions.

Epidermal atrophy was one of the representative side effects caused when a steroid drug was consistently applied onto the skin for 2 weeks or more. Therefore, the epidermal atrophy was checked through a nonclinical trials because the epidermal atrophy was more seriously caused in an animal model having a skin thickness smaller than a human.

Three topical steroid drugs [{Grade 2 (0.05% fluocinonide)-strong preparation; Ox+Steroid 2}, {Grade 4 (0.1% mometasone furoate)-moderate preparation; Ox+Steroid 4}, and {Grade 6 (0.05% desonide)-weak preparation; Ox+Steroid 6}], which were used to treat atopic dermatitis and had different strengths, and the composition of Example 1 (including the compound of Formula 1) were administered to hairless mice with oxazolone (Ox)-induced atopic dermatitis twice a day for 26 days to analyze the results of the side effects.

As one of the typical side effects caused when the topical steroid drugs were applied onto the skin, atrophoderma was checked. As a result, it was revealed that, when the mice were treated with all the three topical steroids (Ox+Steroid 2, Ox+Steroid 4, and Ox+Steroid 6), the skin thicknesses of the hairless mice were smaller than those of normal mice on days 16 and 26 of the application of the topical steroid drugs. On the other hand, it can be seen that the skin thickness increased due to the atopic dermatitis induced by oxazolone (Ox) was rather reduced when the composition of Example 1 (Ox+Compound of Formula 1) was administered (FIG. 7).

Also, a moisture content of the skin, which was highly associated with skin dryness as one of the skin features of patients with atopic dermatitis, was measured. As a result, it can be seen that the moisture content of the skin significantly increased when the mice were treated with the composition of Example 1 (Ox+Compound of Formula 1), compared to the groups (Ox+Steroid 2, Ox+Steroid 4, and Ox+Steroid 6) in which the three topical steroid drugs were administered to the mice. On the other hand, it was confirmed that the moisture content of the skin tended to decrease in all the groups in which the topical steroid drugs were administered, compared to the group in which atopic dermatitis was induced by oxazolone (Ox). This was judged that, when the topical steroid drugs were administered for more than a predetermined period of time, dysfunction of the skin barrier was caused by atrophoderma, resulting in increased side effects in maintaining the moisturizing ability (FIG. 8).

Experimental Example 6: Experiment on the Efficacy of Treatment of Atopic Dermatitis According to the Form of the Formulation Experiments were conducted to observe changes in atopic dermatitis symptoms and changes in the expression level of IgE antibodies that cause atopic dermatitis when the dosage form of the composition for preventing or treating atopic dermatitis is changed.

For nude mouse with atopic dermatitis induced by oxazolone (Ox), ethanol vehicle vehicle were applied once a day to the neck area for 14 days and cream vehicle were applied twice a day to the neck area for 14 days to measure the degree of atopic dermatitis symptoms and the amount of IgE antibody expression. In this case, symptoms of measured atopic dermatitis are excoriation, scaling, edema and erythema.

FIG. 9A is a result of measurement of symptoms of atopic dermatitis after application of ethanol vehicle to nude mouse having atopic dermatitis induced by oxazolone. Specifically, as results of ethanol application (Ox+EtOH), and of the application of ethanol containing 1% by weight of compound of Formula 1 (Ox+Compound of Formula 1), it can be seen that in the case of the ethanol vehicle, the symptoms of atopic dermatitis are not alleviated even when the compound of formula (1) is contained.

FIG. 9B is a result of measurement of symptoms of atopic dermatitis after application of cream vehicle to nude mouse having atopic dermatitis induced by oxazolone. Specifically, as results of the composition of Comparative Example 1 (Ox+Veh) of a cream formulation, a control group (Ox) which does not contain the compound of Formula 1, and of the composition of Example 1 of a cream formulation which contains 1% by weight of the compound of Formula 1 (Ox+Compound of Formula 1), it can be seen that in the case of the cream vehicle, symptoms of atopic dermatitis are remarkably alleviated when the compound of Formula 1 is applied to the composition of Example 1.

FIG. 10A is a result of measurement of the amount of serum IgE antibody expression (Serum IgE) after application of ethanol vehicle to nude mouse having atopic dermatitis induced by oxazolone. Specifically, as results of ethanol application (Ox+EtOH), and of the application of ethanol containing 1% by weight of compound of Formula 1 (Ox+Compound of Formula 1), it can be seen that in the case of the ethanol vehicle, the amount of serum IgE antibody expression is increased rather when the compound of Formula (1) is contained.

FIG. 10B is a result of measurement of the amount of serum IgE antibody expression (Serum IgE) after application of cream vehicle to nude mouse having atopic dermatitis induced by oxazolone. Specifically, as results of the composition of Comparative Example 1 (Ox+Veh) of a cream formulation, a control group (Ox), which does not contain the compound of Formula 1, and of the composition of Example 1 of a cream formulation which contains 1% by weight of the compound of Formula 1 (Ox+Compound of Formula 1), it can be seen that in the case of the cream vehicle, the amount of serum IgE antibody expression is decreased when the compound of Formula 1 is applied to the composition of Example 1.

What is claimed is:

1. A method for preventing or treating atopic dermatitis, comprising a step of administering a compound represented by the following Formula 1 of an effective amount to a subject

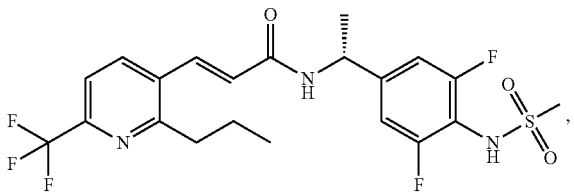

<Formula 1> wherein the atopic dermatitis is mild or moderate (an Investigator's Global Assessment (IGA) score of 2 to 3), and wherein the composition improves one or more parameters selected from the following parameters (a) to (c) associated with atopic dermatitis:

(a) improving an IGA grade of 2 for a patient (with mild symptoms) to grade 1 (almost clear symptoms) or 0 (clear symptoms);

(b) improving an IGA grade of 3 for a patient (with moderate symptoms) to grade 1 (almost clear symptoms) or 0 (clear symptoms); and (c) improving an EASI score and reducing the EASI score by at least 40% or more.

2. The method for preventing or treating atopic dermatitis of claim 1, wherein the compound is administered to patients who suffer from the atopic dermatitis without any specific side effects in the patients who are resistant to or unreactive with steroid drugs or do not sufficiently react with the steroid drugs.

3. The method for preventing or treating atopic dermatitis of claim 1, wherein the patients suffering from the atopic dermatitis have an eczema area and severity index (EAST) of 1.1 to 21.

4. The method for preventing or treating atopic dermatitis of claim 1, wherein the patients suffering from the atopic dermatitis have eruption sites having a body surface area (BSA) of 5% or more.

5. The method for preventing or treating atopic dermatitis of claim 1, wherein the compound is applied onto the skin as a part of a topical composition.

6. The method for preventing or treating atopic dermatitis of claim 5, wherein the composition improves the following parameter (d) associated with atopic dermatitis:

(d) reducing a visual analogue scale (VAS) or a pruritus index represented by pruritus severity.

7. The method for preventing or treating atopic dermatitis of claim 6, wherein the subject of administration of the composition is a child and the EASI score is reduced by at least 60% or more.

8. The method for preventing or treating atopic dermatitis of claim 6, wherein the subject of administration of the composition is an adult and the EASI score is reduced by at least 50% or more.

9. The method for preventing or treating atopic dermatitis of claim 5, wherein the composition comprises 0.1 to 1.5% by weight of the compound of Formula 1.

10. The method for preventing or treating atopic dermatitis of claim 5, wherein the composition is applied onto the skin.

11. The method for preventing or treating atopic dermatitis of claim 5, wherein the composition is percutaneously administered twice a day.

12. The method for preventing or treating atopic dermatitis of claim 5, wherein the composition is administered twice a day for 8 weeks.

13. The method for preventing or treating atopic dermatitis of claim 5, wherein the composition is percutaneously applied twice a day for 8 weeks.

14. The method for preventing or treating atopic dermatitis of claim 5, wherein a change in body temperature is not observed when the composition is administered.

15. The method for preventing or treating atopic dermatitis of claim 5, wherein the composition is administered without side effects of epidermal atrophy even when the composition is repeatedly administered for 4 weeks or more.

16. The method for preventing or treating atopic dermatitis of claim 5, wherein the composition is formulated into a cream, a gel, a patch, a spray, an ointment, a plaster, a lotion, a liniment, a paste, and a cataplasma.

\* \* \* \* \*